(12) United States Patent
Mizrahi et al.

(10) Patent No.: US 7,026,145 B2
(45) Date of Patent: Apr. 11, 2006

(54) PROCESS FOR PRODUCING A PURIFIED LACTIC ACID SOLUTION

(75) Inventors: Joseph Mizrahi, Haifa (IL); Aharon Eyal, Jerusalem (IL); Canari Riki, Jerusalem (IL); Betty Hazan, Jerusalem (IL); John N. Starr, Chaska, MN (US)

(73) Assignees: Cargill, Incorporated, Wayzata, MN (US); CSM NV, Amsterdam (NE)

( * ) Notice: Subject to any disclaimer, the term of this patent is extended or adjusted under 35 U.S.C. 154(b) by 134 days.

(21) Appl. No.: 10/162,935

(22) Filed: Jun. 4, 2002

(65) Prior Publication Data

US 2003/0004375 A1    Jan. 2, 2003

Related U.S. Application Data

(63) Continuation of application No. 09/412,085, filed on Oct. 4, 1999, now abandoned.

(51) Int. Cl.
*C12P 7/56* (2006.01)
(52) U.S. Cl. .......................... 435/139; 562/589
(58) Field of Classification Search ............... 435/139; 562/589
See application file for complete search history.

(56) References Cited

U.S. PATENT DOCUMENTS

| | | | |
|---|---|---|---|
| 1,906,068 A | 4/1933 | Jenemann | |
| 2,712,516 A | 7/1955 | Kool et al. | |
| 4,275,234 A | 6/1981 | Baniel et al. | |
| 4,291,007 A | 9/1981 | Baniel | |
| 4,334,095 A | 6/1982 | Baniel | |
| 4,771,001 A | 9/1988 | Bailey et al. | |
| 5,426,219 A | 6/1995 | Lehnhardt et al. | |
| 5,510,526 A * | 4/1996 | Baniel et al. | 562/580 |
| 5,641,406 A | 6/1997 | Sarhaddar et al. | |
| 5,766,439 A | 6/1998 | Eyal et al. | |
| 5,773,653 A | 6/1998 | Baniel | |
| 5,780,276 A | 7/1998 | Baniel | |
| 5,814,498 A | 9/1998 | Mani et al. | |

FOREIGN PATENT DOCUMENTS

| | | |
|---|---|---|
| EP | 0 750 603 | 1/1997 |
| WO | WO 98/15517 | 4/1998 |
| WO | WO 98/55442 | 12/1998 |
| WO | WO 99/19290 | 4/1999 |
| WO | WO 01/25180 * | 4/2001 |

OTHER PUBLICATIONS

"Cheaper Lactic Acid Ahead? Bowmans Chemicals Purifies Lactic Acid by Solvent Extraction, Simplifies Regular Process", *C & EN*, p. 77 (Jun. 15, 1959).

King, C. Judson, "Separation Processes Based on Reversible Chemical Complexation", *Handbook of Separation Process Technology*, Chapter 15, pp. 760-774 (1987).

Tamada, J. et al., "Extraction of Carboxylic Acids with Amine Extractants. 3. Effect of Temperature, Water Coextraction, and Process Considerations", *Ind. Eng. Chem. Res.*, vol. 29, pp. 1333-1338 (1990).

* cited by examiner

Primary Examiner—Francisco Prats
(74) Attorney, Agent, or Firm—Fish & Richardson P.C., P.A.

(57) ABSTRACT

The present disclosure provides a process for preparing a purified lactic acid solution suitable for use in connection with a source of lactate material a pH within the range of 0.8 to 9.0. The process includes the steps of providing a source of lactate material which includes a calcium salt; acidulating the concentrated broth with sulfuric acid to form an acidulated solution which includes lactic acid and calcium sulfate; reducing an amount of calcium sulfate from the acidulated solution; extracting the acidulated solution with an amine extractant to form a loaded solvent; and back extracting the loaded solvent with an aqueous solvent to provide a purified solution of lactic acid. Optionally, the source of lactate material can be concentrated prior to the step of acidulating. Alternately, the amine extractant can include sulfate anion. The sulfuric anion in the amine extractant can be residual sulfuric acid from the acidulation step. Alternately, the sulfuric acid in the amine extractant can be added during the extraction step, for example, as sulfuric acid.

22 Claims, 4 Drawing Sheets

PROCESS FOR PRODUCING A PURIFIED LACTIC ACID SOLUTION

CROSS-REFERENCE TO RELATED APPLICATION

This application is a continuation of application Ser. No. 09/412,085, filed Oct. 4, 1999, now abandoned the specification of which is incorporated by reference in its entirety.

FIELD OF THE INVENTION

The present invention relates to lactic acid processing. It particularly concerns a method for obtaining a purified lactic acid solution from a source of lactate material having either a neutral or low pH, and the resulting products.

BACKGROUND

The potential of lactic acid as a commodity chemical, for example for use in the production of various industrial polymers, is known. The use of lactic acid as a commodity chemical is particularly of interest because polylactic acid and many of its products are biodegradable. Additionally, lactic acid can be produced by fermentation, using renewable carbon sources.

Low pH fermentation is a process under investigation for improving the commercial viability of lactic acid production. In contrast to neutral pH fermentation (e.g., pH in the range of 5.0 to 8.0, inclusive, more typically 5.0 to 7.0, inclusive) in which the lactate material is mainly present as a lactate salt, lactate material formed using a low pH fermentation (e.g., at a pH below 5.0, typically below 4.8, more typically below 4.3) includes a significant amount of the free acid form. Thus, isolating lactic acid from an aqueous solution having a pH below 5.0 tends to reduce the need for acidulation technology typically necessary for isolating lactic acid from an aqueous solution having a pH above 5.0.

Many acidification technologies have significant capital costs or operating costs; consume acidification reagents; and/or result in the consumption of reagents and formation of by-product salts. Therefore, there is an interest in developing organisms that are capable of retaining high productivity at pH ranges of 5.0 or lower.

In addition to the effort to develop organisms having high productivities at a low pH, there is an effort to increase the use of mixed sugar streams during fermentation. Unlike traditional fermentation media, which typically includes a purified sugar stream such as dextrose as a carbon source, mixed sugar streams include combinations of hexoses, hexuloses, and pentoses such as dextrose, galactose, fructose, arabinose, and xylose. Mixed sugar streams are a lower cost carbon source that can be obtained, for example, by enzymatic or acid hydrolysis of cellulose and hemicellulose. U.S. Pat. Nos. 5,562,777, 5,620,877 and 4,350,766 discuss methods for making mixed sugar streams. U.S. Pat. Nos. 5,798,237 and 5,789,210 discuss use of these streams as a carbon source for fermentation. The disclosure of these five patents are incorporated by reference herein.

Although mixed sugar streams provide a relatively low cost carbon source, mixed sugar streams typically have more impurities, such as lid than conventional dextrose streams. Not only do the impurities increase the burden on the microorganism, which must tolerate the impurities, the impurities also must be separated from the fermentation broth and the lactate material. Therefore, a separation process tat is capable of reducing the presence of impurities due to the use of mixed sugar streams, or other carbohydrates sources, is also desirable.

SUMMARY

The present disclosure provides a process for preparing a purified lactic acid solution suitable for use in connection with a source of lactate material having either a neutral pH (e.g., between about 5.0 and 8.0, inclusive, more typically between about 5.0 and 7.0, inclusive) or a low pH (e.g., below 5.0, typically below 4.8, more typically below 4.3).

One preferred process disclosed herein includes steps of providing a source of lactate material which includes calcium lactate; concentrating the source of lactate material to form a concentrated solution; acidulating the concentrated solution with sulfuric acid to form an acidulated solution which includes lactic acid and calcium sulfate; reducing the amount the calcium sulfate in the acidulated solution; extracting the acidulated solution with an extractant to form a loaded solvent; and stripping the loaded solvent to provide a purified solution of lactic acid, for example, by back extraction with an miscible aqueous solution. The process steps do not have to be performed in the order recited. For example, the step of concentrating can be performed before and/or after the step of acidulating.

Alternately, the process can be applied in a manner including the steps of providing a source of lactate material which includes calcium lactate; acidulating the source of lactate material with sulfuric acid to form an acidulated solution which includes lactic acid and calcium sulfate; reducing the amount of calcium sulfate in the acidulated solution; combining the acidulated solution with an extractant to form an extraction solution wherein the extraction solution includes sulfuric acid, extracting the acidulated solution with the extraction solution to form a loaded solvent; and stripping the loaded solvent to provide a purified solution of lactic acid. The sulfuric acid in the extraction solution can be residual sulfuric acid from the acidulation step. Alternately, sulfuric acid can be added to the extraction solution prior to or during the extraction step.

Optionally, the process can be applied in a manner that includes a step of reducing the amount of impurities having a molecular weight of about 5,000 Da and greater in the source of lactate material prior to the step of concentrating. Preferably, the source of lactate material includes a fermentation broth and calcium lactate is formed a result of using calcium carbonate or calcium hydroxide as pH controlling agents during the fermentation.

DETAILED DESCRIPTION

Figure 1:
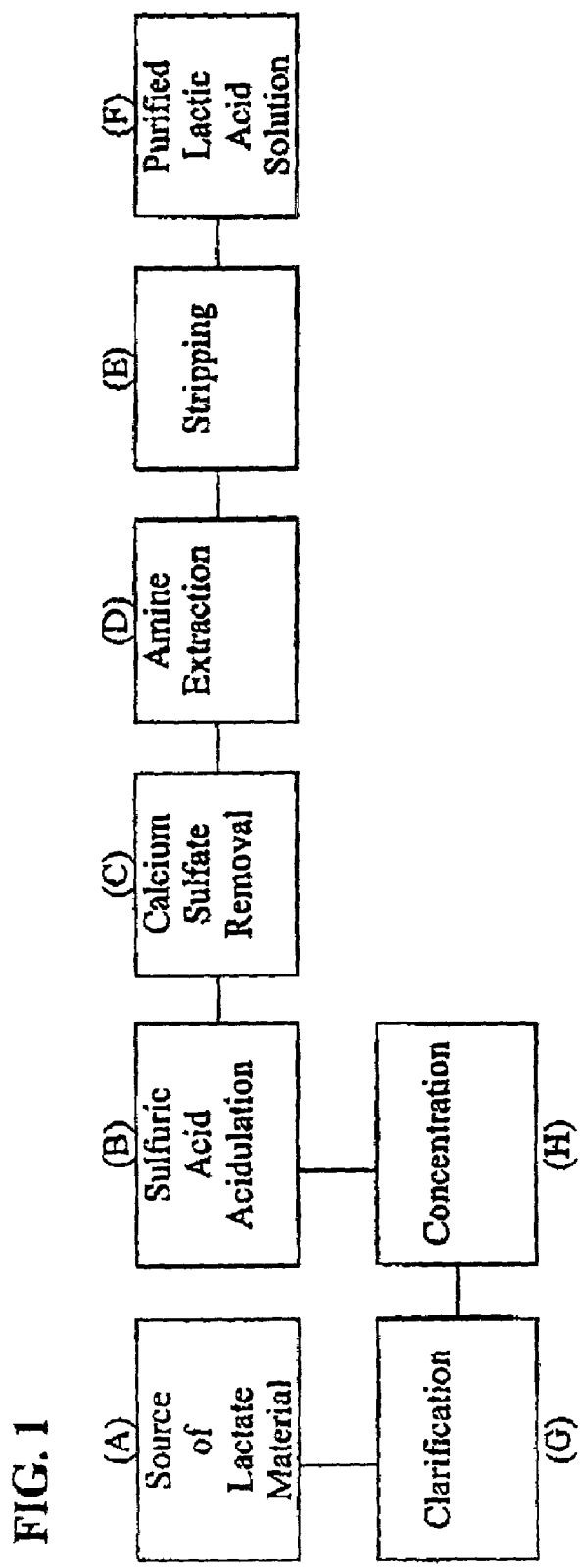
FIG. 1 is a process flow chart showing a process for generating a purified lactic acid solution.

The invention provides a process for obtaining a purified lactic acid solution from a source of lactate material having either a neutral or low pH. Typically, the source of lactate material includes a fermentation broth. As used herein, "fermentation" refers to any metabolic process that produces a useful product by the mass culture of microorganisms. A variety of microorganisms are suitable for use in the fermentation process, for example, bacteria, yeast and fungi. The term "lactate material" herein refers to 2-hydroxypropionate in either its bee acid or salt form and also to lactic acid oligomers, such as lactoyl lactate, in their free acid and/or salt form. The terms "lactic acid" and "free lactic acid" are employed interchangeably herein to refer to the acid form, e.g., 2-hydroxypropionic acid, also called the "undissociated" form and lactic acid oligomers in the acid form. The salt or "dissociated" form of lactate is specifically referred to herein as a "lactate salt," for example, as the sodium (or calcium) salt of lactic acid or sodium lactate (or calcium lactate) and the salt or "dissociated" for of lactic acid oligomers. "Nutrient medium" refers to media in the form originally provided to the microorganism for fermentation and typically includes a carbon source, a nitrogen source and other nutrients. The term "fermentation broth" refers to a mixture that includes lactate material (e.g., free lactic acid and lactate salt) produced after some or all of the originally provided nutrients have been consumed and fermentation products including lactate material have been excreted into the media by the microorganism. The fermentation broth can include recycle streams from other processes, including the process described herein. The fermentation broth is also referred to as a "source of lactate material." "Clarified solution" refers to the source of lactate material or fermentation broth after at least some impurities have been removed.

Herein the terms "polylactic acid" or "polylactate" are intended to refer to any polymer comprising at least 50% by wt. polymer units of lactic acid residue or lactide residue. Thus, the two terms include within their scope polylactides. The terms "polylactic acid" and "polylactate" are not meant to specifically identify the polymerized monomer, for example whether the material polymerized was lactide (lactic acid dimer) or lactic acid itself.

By convention, the amount of lactate material in a solution, such as a fermentation broth, can be represented by the weight percent of lactate material present calculated as if it was all in the undissociated or acid form; or the weight percent of lactate material present in the solution calculated as if it was all in the dissociated or salt form. When the amount of lactate material in a solution is provided herein, it generally represents the weight percent of lactate material present if calculated as it was all in the undissociated or acid form, unless otherwise noted.

I. Overview

The process described herein provides a method for obtaining a purified lactic acid solution from a source of lactate material. Suitable sources of lactate material include, but are not limited to, a fermentation broth, a recycle stream from polylactic acid production which contains lactate material, or recycled polylactic acid (e.g., post-consumer waste or production scraps) that has been hydrolyzed to form a solution containing lactate material. Typically, the source of lactate material is a fermentation broth. (The term fermentation broth may refer to a fermentation broth which includes recycle streams from the process described herein or other processes.) Therefore, the discussion will emphasize the use of a fermentation broth as a source of lactate material. However, the techniques described herein are not so limited in application.

Typically, the source of lactate material includes compounds other than lactic acid, referred to as impurities. For example, fermentation broth may include both lactic acid and lactate salt, collectively referred to as lactate material, along with cellular debris, residual carbohydrates, nutrients and other impurities. Generally, for commercial purposes, it is desirable to have a solution that includes lactic acid in an aqueous carrier with less than about 1.0 g/L to about 5.0 g/L impurities, more preferably less than about 0.005 g/L to about 1.0 g/L impurities. However, the acceptable concentration of impurities can vary depending on the commercial use of the solution and the concentration of lactic acid within the solution. Thus, the process provides a method for obtaining a purified lactic acid solution from a source of lactate material such as a fermentation broth. As used herein, the phrase "purified lactic acid solution" refers to a solution which contains between about 5 wt % to about 90 wt % lactic acid, more typically between about 10 wt % to about 90 wt % lactic acid, most typically between about 20 wt % to about 50 wt % lactic acid, an aqueous carrier and no more than about 1.0 g/L to about 5.0 g/L impurities, more preferably no more than about 0.005 g/L to about 1.0 g/L impurities, such as proteins, carbohydrates, cellular debris, etc.

One preferred process is shown in FIG. 1. In this process, a source of lactate material which includes calcium lactate (A) is concentrated (H) to form a concentrated solution. The concentrated solution is acidulated (B) with sulfuric acid to form an acidulated slurry which includes lactic acid and calcium sulfate. The amount of calcium sulfate in the acidulated slurry is reduced (C) and the acidulated solution is then extracted (D) with an extractant to form a loaded solvent. The loaded solvent is stripped (E) to provide a purified solution of lactic acid (F), for example, by back extraction with an immiscible aqueous solution.

Figure 2:
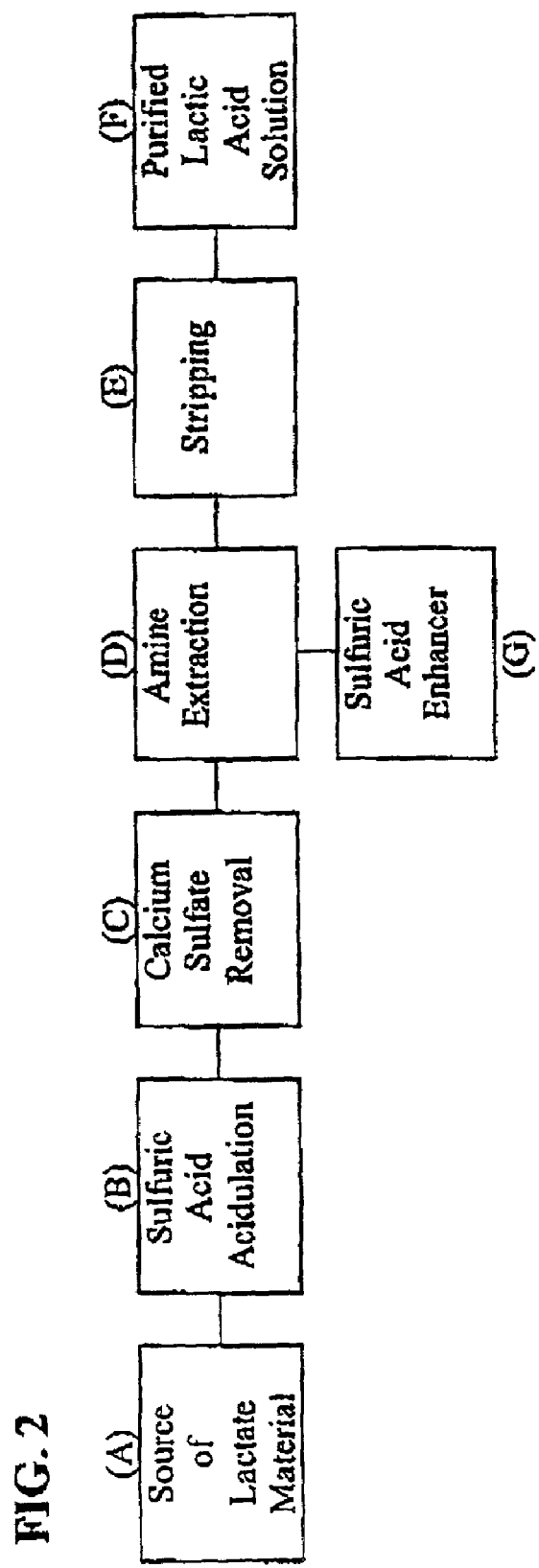
FIG. 2 is a process flow chart of an alternate process for generating a purified lactic acid solution.

Alternately, the process can be applied in a manner shown in FIG. 2, including the steps of (A) providing a source of lactate material which includes calcium lactate; (B) acidulating the source of lactate material with sulfuric acid to form an acidulated solution which includes lactic acid and calcium sulfate; (C) reducing the amount of calcium sulfate in the acidulated solution; (D) combining the acidulated solution with an extractant to form an extraction solution wherein the extraction solution includes sulfuric acid (G); (D) extracting the acidulated solution with the extraction solution to form a loaded solvent; and (E) stripping the loaded solvent to provide a purified solution of lactic acid (F).

The process includes the steps of acidulating a source of lactate material (which includes calcium lactate) with sulfuric acid to form an acidulated solution containing lactic acid and calcium sulfate (gypsum) in combination with the steps of gypsum filtration, amine extraction and stripping the extractant, for example by aqueous back extraction, to obtain a purified lactic acid solution. In one version of the process, (shown in FIG. 1) the process includes a step of concentrating the source of lactate material prior to acidulation (FIG. 1(H)). In another version, sulfuric acid is included in the amine extractant (See FIG. 2). The process is, suitable for processing a source of lactate material, such as a fermentation broth, having a pH of at least 0.8 and less than 9.0. Additionally, the process is suitable for processing a fermentation broth which includes additional impurities due to the use of a mixed sugar carbon source.

A "clarification" process may be performed to reduce the presence of suspended cell mass and other high molecular weight compounds (e.g., impurities having a molecular weight of about 5,000 Da and greater, preferably about 40,000 Da and greater) in the source of lactate material. (See FIG. 1(G)). Preferably, the step of clarification includes cross-flow filtration. More preferably, a two-stage cross-flow filtration technique is employed.

A strong acid, such as sulfuric acid, is then added to the clarified solution in an amount sufficient to convert most of the lactate material in the broth (e.g., at less about 90 wt %, more preferably at least about 95 wt % of the lactate material) to an undissociated acid form. (FIG. 1(B) and FIG. 2(B)) Preferably, the source of lactate material includes calcium lactate such that the acidulation process results in the formation of lactic acid and calcium sulfate (gypsum). Gypsum is only slightly soluble in water and is easily removed from the broth by known techniques. (FIG. 1(C) and FIG. 2(C)).

Even after the sulfate salt is removed from the solution, some low molecular weight impurities (e.g., impurities having a molecular weight of about 100 Da to about 500,000 Da, more typically about 100 Da to about 300,000 Da, such as amino acids and carbohydrates), may remain suspended or dissolved in the solution. The purified solution of lactic acid is prepared by extracting the acidulated solution with all extractant containing a water insoluble amine (FIG. 1(D) and FIG. 2(D)) and stripping the lactic acid from the amine solvent, for example by back extracting the lactic acid into a liquid phase that is immiscible with the extracting solvent (FIG. 1(E) and FIG. 2(E)), preferably an aqueous phase.

Optionally, a concentration step (FIG. 1(H)) may be performed after and/or after the clarification step and before and/or after the acidulation step. The source of lactate material is preferably concentrated at an elevated temperature to obtain a concentrated solution containing lactate material having a concentration of lactate material of about 12–60 wt %. See FIG. 1(H).

Alternately, sulfuric acid may be included in the amine extractant as an enhancer. The sulfuric acid can be present in the amine extract as residual sulfuric acid from the acidulation step; added during the amine extraction step; or added to the amine extractant prior to or during the extraction step. See FIG. 2(G).

II. Selected Features of the Process

The process described herein is suitable for obtaining a purified solution of lactic acid from a source of lactate material having a pH between 0.8 and 9.0. Thus, the process can be used in connection with a neutral fermentation process and then converted to a low pH fermentation process, or vice versa, without changing equipment. At most, some stages may have excess capacity, e.g, excess acidulation capacity or excess capacity during gypsum filtration when converting from a neutral pH fermentation to a low pH fermentation. In contrast, many existing methods are not effective for use with sources of lactate material having a variety of pH. Thus, in many existing methods the entire process must be altered, and new equipment installed, if the end user converts from a neutral fermentation process to a low pH fermentation process, or vice versa.

Concentrating the source of lactate material prior to liquid-liquid extraction tends to increase the yield of lactic acid recovered during extraction with an organic solvent compared to extraction of a dilute source of lactate material. Concentrating the source of lactate material alters the ratio of organic phase to aqueous phase during liquid-liquid extraction. It is speculated that the change in phase ratios during the extraction results in higher recovery of lactic acid.

Combining a sulfuric acid acidulation step with an amine extraction tends to result in improved partitioning of the lactic acid in the organic phase at low (e.g., no more than about 10 wt %) lactic acid concentrations in the aqueous phase. It is speculated that residual sulfuric acid acts as an enhancer during the amine extraction step. Additionally, residual sulfuric acid in the amine extractant tends not to partition into the aqueous phase during subsequent aqueous back extraction. Consequently, sulfuric acid is not likely to contaminate the end product. Because the process purifies lactic acid using a liquid-liquid extraction process, it is suitable for processing lactic acid formed by fermentation using mixed sugar streams. In contrast, other purification processes, such as water splitting electrodialysis are less suitable for use with lactic acid formed by fermentation using mixed sugar streams because the impurities in the fermentation broth due to the mixed sugar streams tend to foul the membranes.

The process does not require the relatively expensive equipment used in many existing commercial processes. For example, equipment used in $CO_2$ extraction (U.S. Pat. No. 5,510,526) must be able to withstand the pressure of the carbon dioxide and be capable of mixing and coalescing four phases (gas, solid, and two liquid phases) and recycling the carbonate or bicarbonate salt back to the fermentation vessel. Membranes and membrane modules used in water splitting electrodialysis are expensive and the operating costs for water splitting electrodialysis (e.g., electricity) can be expensive. Ion exchange processes, particularly when used in connection with large scale process using a neutral pH broth, require multiple beds with large resin volumes. Regeneration of cation exchange resins to a protonated form requires excess hydrochloric acid or another strong mineral acid and creates water soluble salt stream that requires disposal. Landfilling a water soluble salt typically requires the evaporation of water to crystallize the salt, thus increasing disposal costs. Before and after each regeneration step, the resin is typically rinsed. The rinse water tends to add more water to the system and thus increases the water evaporation load.

In contrast, the process according to the preferred techniques described herein can be performed using equipment that is relatively simple and inexpensive, e.g., an acidulation vessel and/or a gypsum crystallization vessel can be less complex and less expensive as compared to a $CO_2$ vessel or equipment needed for water splitting electrodialysis. The process is also easily integrated with other lactic acid production processes. For example, the loaded solvent from the process described in U.S. Pat. No. 5,510,526, incorporated by reference herein, can be used as an extractant in the present process. The process can also be used to purify contaminated side streams from known polymerization processes.

III. Other Processes

Many existing processes are not suitable for use with a sources of lactate material having a broad range of pH values. For example, although water-splitting electrodialysis is an efficient method for acidulation of lactic acid from a neutral fermentation broth, it tends to be less effective for acidulation of lactic acid from a low pH fermentation broth. In water-splitting electrodialysis, lactate salt is converted to free lactic acid and a corresponding base by driving (using electrical current) lactate anion and corresponding cation across anion and cation selective membranes, respectively. A bipolar membrane, which includes an anion and cation selective membrane, is used to split water into a proton and hydroxyl ion. The proton is combined with the lactate anion to form free lactic acid, and the hydroxyl ion is combined with the cation to form a cation hydroxide salt. Water splitting electrodialysis for lactic acid acidulation is discussed in U.S. Pat. No. 5,776,439. Equipment for water-splitting electrodialysis is discussed in U.S. Pat. Nos. 5,198,086; and 4,7540,281. The disclosures of these patents are hereby incorporated by reference. Because existing free lactic acid (present in a low pH fermentation broth) is not influenced by the electrical field, it does not pass through the anion selective membrane. Therefore, free lactic acid existing in the fermentation broth tends to remain with the neutral impurities in the broth. Thus, the free lactic acid originally existing in the fermentation broth may not be recovered.

Ion exchange processes are effective for acidulation of a low pH broth but tend to be less efficient for acidulation of neural pH broth. In ion exchange processes, fermentation broth is contacted with a protonated cation exchange resin. The proton from the resin and cation of the salt are exchanged to form lactic acid. The cation from the salt remains on the resin. In low pH broth, the lactate material is nearly all in the free lactic acid form. Thus, the resin can process many volumes of broth before it needs to be regenerated. However, when the fermentation broth is at a neutral pH, only a few volumes of broth can be processed before regeneration is required. Consequently, efficiency is decreased because the resin needs to be regenerated frequently.

Carbon dioxide ($CO_2$) assisted liquid-liquid extraction is an acidulation technique designed to recover lactate salt from a neutral fermentation broth, (U.S. Pat. No. 5,510,526). Basically, in $CO_2$ assisted liquid-liquid extraction, lactate salt is converted to free lactic acid by $CO_2$ chemistry and then the newly converted lactic acid is extracted from the broth. $CO_2$ assisted liquid-liquid extraction tends to be less efficient for use in connection with a low pH fermentation broth as compared to a neutral pH fermentation broth. At a low pH, lactate salt may not be converted to free lactic acid via the $CO_2$ chemistry because the concentration of free lactic acid in the organic phase may be already greater than the lactic acid concentration achievable through the $CO_2$ chemistry.

Extractive fermentation is a method by which free lactic acid is recovered from fermentation broth by liquid-liquid extraction or adsorption and the lactate salt is recycled back to the fermentation to help control the pH of the fermentation. See, e.g., PCT 99/19290 and U.S. Pat. No. 5,786,185, incorporated by reference herein. Extractive fermentation tends to be more efficient when the fermentation broth has significant amounts of both free lactic acid and lactate salt (i.e., at low pH). However, when the lactate material is present mainly as lactate salt (i.e., at neutral pH), the advantages of extractive fermentation tend to decrease. High concentrations of lactate salt in the recycle stream may be inhibitory to the microorganisms in the fermentor. Process productivity, as measured by pounds of free lactic acid recovered per gallon of fermentation broth per hour, tends to be low because of the low amount of free lactic acid recovered per gallon. Thus, large amounts of fermentation broth must be processed to achieve a high capacity plant. On the other hand, when free lactic acid is mainly present in the fermentation broth (i.e., at a low pH), there is little incentive to recycle the lactic acid depleted stream back to the fermentor. The recycle stream increases the complexity of the process, adds impurities into the system, and provides little benefit since the free lactic acid concentration is already high.

IV. Lactic Acid

Prior to discussing the process, a brief discussion of some aspects of lactic acid will be provided.

a. pH and Lactic Acid Composition

In an aqueous solution, lactic acid (referred to by abbreviations HLa and/or LaH) dissociates into a proton, $H^+$, and a lactate anion, $La^-$ (sometimes referred to herein as dissolved lactate salt when another source of cation is present, typically from the buffering salt). The amount of dissociation at equilibrium is related to the pH of the solution and the $pK_a$ of lactic acid. Equation 1 below demonstrates the general relationship between pH, $pK_a$, and degree of lactic acid dissociation, where $[La^-]$ and $[HLa]$ are the thermodynamic activities of the lactate anion and the free lactic acid, respectively.

$$pH = pK_a + \log\frac{[La^-]}{[HLa]} \mid \qquad \text{Equation 1}$$

As shown in equation 1, about half the lactate material is in its dissociated form when the pH equals the $pK_a$ of the acid. At pH values greater than the $pK_a$, the majority of the lactate material is in dissociated form (also called the lactate anion or lactate salt form). On the other hand, at pH values less than the $pK_a$, there is a significant amount of lactate material in the undissociated form (also called the acid form).

The $pK_a$ of the lactate material can vary. For example, at 25° C. the $pK_a$ of lactic acid is 3.86, whereas at 5° C., the $pK_a$ is about 3.89. Furthermore, it has been noticed that the $pK_a$ of lactic acid tends to decrease as the concentration of lactic acid in solution increases, and tends to increase as the concentration of lactic acid in solution decreases. However, the $pK_a$ of lactic acid is generally within the range of about 3.4 to about 3.9.

As indicated above, the amount of free lactic acid present in a solution is a function of both the pH of the solution and the overall concentration of lactate material (i.e. lactic acid plus dissolved lactate salt) in the mixture. Thus, specifying these two parameters for a given solution (e.g., a fermentation broth), effectively specifies the free lactic acid concentration. The lower the solution pH, the higher the percentage of the lactate material which is present in the free acid form. Again, if the medium (solution or mixture) pH is equal to the $pK_a$ of lactic acid (which is about 3.8 at 25° C.), 50% of the lactate material is present in the free acid form.

b. Chirality

Lactic acid has a chiral center and is found in both the D and L forms. The chiral purity of the lactic acid can be important in some industrial applications, see for example U.S. Pat. Nos. 5,142,023; 5,338,822; 5,484,881; and 5,536,807, incorporated by reference herein. There are bacteria, for example from the *Lactobacillus genus*, that can make either the D-lactic acid or the L-lactic acid. However, bacteria strains typically produce predominantly one enantiomer. Indeed, fermentation broths with high chiral purity (90% or greater) of lactic acid can be readily obtained. This chirality is obtained from the metabolism of dextrose or other carbohydrates by microorganism cells during fermentation. For example, *Lactobacillus bulgaricas* and *Lactobacillus coryniformis* typically make the D-lactic acid enantiomer almost exclusively. *Lactobacillus casei* has been found to produce, in majority, L-lactic acid.

The chiral purity of the lactic acid can influence on the properties of a polylactic acid polymer. For example, the ability of the polymer to crystallize is affected by the chiral purity of the polymer; See for example U.S. Pat. Nos. 5,484,881; 5,585,191; and, 5,536,807. (Each of these references are incorporated herein by reference.) Polymers with a particular crystallinity may be desired in a particular industrial application. For example, polymer crystallinity can affect the heat distortion temperature of the polymer. The crystallinity of the polymer can also affect the storage, transfer and processing of polylactic acid resins into fibers, non-woven fabrics, films, and other end products.

Lactic acid currently used in food applications has chiral purity requirements greater than 95% chiral purity, generally with a preference for the "L" form. The chiral purity of lactic acid is also important for end products such as pharmaceuticals and other medical devices where lactic acid is a starting material. Herein the term "95% chiral purity" means 95% of the lactic acid/lactate content is one of two possible enantiomers. (Thus, the composition could alternatively be characterized as 10% racemic or 90% optically pure.) In other applications, an optical purity of the lactic acid of at least 50%, more preferably at least 75% and most preferably at least 90% may be desirable.

V. Fermentation

Although the process is suitable for use with a variety of sources of lactate material, the process will be described in connection with a fermentation broth as a source of lactate material.

Fermentation can be conducted using microorganisms such as bacteria, fungi or yeast, capable of forming lactic acid upon metabolizing a carbon source. Such lactate material producing organisms are known. Typically, bacteria of the family *Lactobacillaceae* are employed. As to fungi, those of the family *Rhizopus* can be employed. Suitable yeast include *Saccharomyces* and *Kluveromyces*, for example, *Saccharomyces cerevisiae*.

Fermentation is typically conducted at a temperature suitable for the particular organism being used, typically between about 30° C. and about 60° C. for bacterial fermentations and between about 20° C. and about 45° C. for yeast fermentations. For fungal fermentations, the temperature may vary widely but are often within the range of about 25° C. to about 50° C.

The nutrient media typically contains a carbon source. Generally, the carbon source includes carbohydrate containing raw materials. Many by products of agricultural processes provide inexpensive carbon sources. Examples of suitable carbon sources include molasses; cane or beet sugar; corn, potato or rice starch and hydrolysates; whey and whey permeate. Suitable solutions containing sugars such a glucose and sucrose can also be prepared. For fungal fermentations, raw materials such as barley, cassava, corn, oats and rice may be used as a carbon source.

Typically, the nutrient media also contains a nitrogen source. Preferably the nitrogen source includes a combination of organic and inorganic nitrogenous compounds. Examples of suitable nitrogen sources include yeast exact, corn steep liquor, soy hydrolysate, malt sprouts and ammonium sulfate.

The pH of the fermentation broth during the incubation step can be expressed in terms of the "average incubation pH" or the "final incubation pH." If fermentation is carried out to a point where pH and/or lactic acid concentration inhibits further lactate production, the "average incubation pH" is determined based on an average of the pH values measured at ten (10) or more equal time intervals over the time period necessary to produce 90% of the limiting lactate concentration.

As used herein, the "limiting lactate concentration" is the lactate concentration (concentration of undissociated and dissociated lactic acid) under a given set of incubation conditions (nutrient medium, temperature, degree of aeration) at which pH and/or lactic acid concentration generated by the fermentation inhibits further lactate production. As used herein, the term "limiting incubation pH" means the pH of the fermentation broth for a given set of incubation conditions at which the pH and/or lactic acid concentration inhibits further lactate production. Inhibition of lactate production is considered to have occurred when the amount of lactate produced in a batch fermentation does not increase by more than about 3% upon further incubation for a period of up to about twelve (12) hours under the same conditions. This definition presumes that sufficient nutrients for lactate production are still available in the fermentation broth and applies to both batch and continuous operations.

Alternately, the fermentation process can be run in a continuous fashion wherein a limiting lactate concentration is not reached. Generally, when fermentation is run in a continuous fashion, there is an initial "startup phase" where the pH of the fermentation broth fluctuates, as does the nutrient concentration and lactate concentration. However, after a period of time, steady state conditions are achieved. Typically, the response time to reach a steady state is at least about 3 to about 5 times the residence time, depending on the dilution rate. Under "steady state conditions" processing variables such as pH, lactate concentration and nutrient concentration do not change significantly over time. For example, under steady state conditions, the pH of the fermentation broth generally does not fluctuate by more than about 0.5 pH units, more preferably about 0.2 pH units during the course of one residence time. As used herein the term "residence time" or "residence period" refers to the average time that a molecule is present in the fermentation tank. The residence time can be determined by calculating the ratio of the broth volume over the flow rate of what all streams entering and exiting the fermentor. Under steady state conditions, the flow rate of all streams entering the fermentor is equal to the flow rate of all streams exiting the fermentor. For example, in a tank having a volume of 100,000 gallons and a flow rate of 12,500 gallons per hour, one residence time equals 8 hours. Typically, for commercial scale fermentation, one residence time is about 2 to about 10 hours, more typically about 5 to about 7 hours. Under steady state conditions, lactate concentration generally does not fluctuate by more than about 2%, more preferably no more than about 1% and nutrient concentration by no more and about 0.3%, more preferably no more than about 0.1% during the course of one residence time. Thus, in a continuous system, "average incubation pH" is determined based on an average of the pH values measured at ten (10) or more equal time intervals over the course of the fermentation after steady state conditions have been achieved.

As referred to herein, the "final incubation pH" is the pH of the fermentation broth at the point that growth and/or lactate material production by the microorganism ceases. The cessation of growth and/or lactate material production may be the result of a change in reaction temperature, the exhaustion of one or more necessary nutrients in the fermentation broth, a deliberate change in pH, or the separation of the fermentation broth from the bacterial cells. In those instances in which fermentation is deliberately stopped by the addition to the fermentation broth of sufficient acid or base to stop lactate production, the final incubation pH is defined to be the pH of the nutrient medium just prior to the addition of acid or base. Alternatively, growth and/or lactate material production may stop due to the accumulation of one or more fermentation products and/or a change in broth pH resulting from the production of fermentation products, i.e., the fermentation reaction has reached a self limiting point for the given set of incubation conditions. It is quite common for bacterial fermentations which produce an organic acid such as lactic acid to be subject to end-product inhibition.

a. Neutral pH Fermentation

The source of lactate material can have a neutral pH, for example, a broth from a neutral pH fermentation. A large number of strains of microorganisms are known and used for production of lactic acid at a neutral pH. The most important of these are homofermentative lactic acid bacteria of the genera *lactobacillus, streptococcus* and *pediococcus*. Typically, optimal productivity for these microorganisms is achieved at a pH between about 5.0 and 8.0, more typically between about 5.0 and 7.0 (a "neutral pH"). See, for example, U.S. Pat. No. 5,510,526, incorporated by reference herein.

Because the fermentation broth typically becomes more acidic as lactic acid is produced, a neutral pH is typically maintained by adding a neutralizing agent, such as alkali- or alkali earth hydroxide (calcium hydroxide), calcium carbonate, milk of lime, ammonia water or ammonia gas to the fermentation broth. When added to the fermentation broth, the cation from the neutralizing agent combines with the dissociated lactic acid to form a lactate salt.

Preferably, a calcium base, such as calcium carbonate or calcium hydroxide, is added to the fermentation broth as a neutralizing agent such that calcium lactate is formed. Calcium bases tend to be more acceptable to many lactate producing microorganisms when compared to other neutralizing agents. Additionally, calcium bases tend to be less expensive than other neutralizing agents. However, many existing process are not well suited for processing solutions which contain calcium base. For example, calcium base tends to clog membranes in electrodialytic water splitting—based processes. $CO_2$ liquid-liquid exaction tends to be inefficient when used in connection with calcium lactate containing solutions (Lightfoot et. al. Ind. Eng. Chem. Res. 1996, 35,1156). When calcium base is used in connection with a cation-exchanger-based acidulation process, a large excess of acid is required to regenerate the cation resin. In contrast, the present process is suitable for treating solutions which contain calcium base. In fact calcium base is a preferred neutralizing agent.

Neutral pH fermentation can be performed as a batch process or a continuous process. In a batch process, an appropriate nutrient media is dispensed into a fermentation vessel. Generally, the nutrient media includes a suitable carbohydrate source along with a suitable complex nitrogen source to supply various amino acids, vitamins, minerals and other growth factors. The nutrient media is then inoculated with the desired microorganism. The temperature and pH of the fermentation vessel is maintained within an optimal range (depending on the microorganism or strain) until the carbohydrate supply is exhausted. Preferably, a neutral pH is maintained by the addition of a neutralizing agent. After the carbohydrate supply is exhausted the product (lactate material) is purified from the fermentation broth.

In a continuous process, nutrient media, microorganisms and other additives (such as a neutralizing agent) are added to the fermentor and fermentation broth is removed from the fermentor in such a manner that a limiting lactate concentration is not obtained. Typically, the nutrient media, microorganisms and other additives are added in specified amounts at a specified rate or at specified intervals. Fermentation broth is removed at a rate that compensates for the addition of these materials such that a steady state condition is obtained. Under steady state conditions, the fermentation broth is removed at a rate equal to the flow rate of the nutrient media, microorganisms and additives added to the fermentor.

Preferably, a multi-stage continuous fermentation process is used in which multiple fermentation vessels are used. Fresh media, microorganisms and the like are added to a first vessel. The fermentation broth from the first vessel is then transferred to a second vessel and the fermentation broth from the second vessel is transferred to a third vessel, and so on. Typically, the concentration of lactate material increases and the concentration of the carbon source decreases with each stage such that the first vessel has the highest concentration of carbon source and the lowest concentration of lactic acid and the final vessel has the highest concentration of lactate material and the lowest concentration of carbon source. Typically, a multi-stage process having about 2 to about 8 stages is used.

In some cases, the calcium lactate may crystallize during fermentation because the calcium lactate concentration may exceed the solubility limit of calcium lactate. Alternatively, the fermentation broth may be cooled to cause the crystallization of calcium lactate. The crystallized calcium lactate may be separated from the fermentation broth and used as a source of the lactate material. The mother liquor (filtrate) from the calcium lactate separation can be recycled back to the fermentor.

b. Low pH Fermentation

The process is also suitable for purifying lactic acid from a source of lactate material having a low pH, for example a low pH fermentation broth. In contrast to neutral pH fermentation, the lactate material produced in a low pH fermentation (i.e., in an aqueous solution having a pH below 5.0, preferably below 4.8, more preferably below 4.3) includes a significant amount of lactate material in the free acid form. Thus, isolating lactic acid from an aqueous solution having a pH below 4.5 tends to eliminate significant costs associated follow up processes, such as acidulation, that are typically necessary with neutral fermentation processes. Furthermore, even if acidulation is conducted, substantially less energy and/or chemicals, such as acid, is typically required per unit of lactate material formed in the fermentation. Therefore, there is an interest in developing organisms that retain high productivity at a "low pH." As used herein, "low pH" refers to a solution having a pH on the order of 5.0 or below, preferably 4.8 or below, more preferably about 4.3 or below and typically about 2.5 to 4.2. Even though the microorganism is capable of retaining high productivity at a low pH, a neutralizing agent, such as calcium hydroxide or calcium carbonate, may be added to the fermentation broth to maintain the desired, albeit low, pH.

Organisms capable of metabolizing a carbohydrate source to form lactic acid at a low pH are known. For example, low pH fermentation can be performed using acid-tolerant bacteria, such as acid-tolerant homolactic bacteria. The term "acid-tolerant" refers to bacteria which are capable of producing lactate material at a pH sufficient to furnish a substantial portion of the lactate material in the free acid form. This is described, for example, in PCT 99/19503 (discloses fermentation of carbohydrates to lactic acid at a final pH of about 3.8 with a lactic acid concentration of about 70 to 80 g/L using an acid-tolerant *Lactobacillus* isolated from a natural source), incorporated by reference herein. Alternately, low pH fermentation can be performed using fungi or yeast. For example, PCT 99/14335 discloses fermentation of carbohydrates to lactic acid at a final pH of about 2.8 with yeast strains transformed with at least one copy of lactate dehydrogenase to allow the production of lactic acid from pyruvate, hereby incorporated by reference.

Low pH fermentation can be performed as a batch or continuous process, described above.

V. Solution Clarification

The source of lactate material typically contains impurities that may need to be removed to produce a commercially useful purified lactic acid solution. For example, a source of lactate material obtained from either neutral or low pH fermentation typically contains dissociated and undissociated lactate material (i.e., both free acid and salt), unconverted starting material (carbon source), heavy metals, metabolic by products, cells, cell fragments and inorganic salts. Processing is typically required to obtain a purified lactic acid solution.

Accordingly, the process may include a "clarification" step in which the amount of suspended cell mass and/or other high molecular weight debris in the source of lactate material is reduced. The term "high molecular weight debris" refers to impurities having a molecular weight of about 10,000 Da to about 500,000 Da, more preferably about 40,000 Da to about 500,000 Da, such as macroscopic solids, undissociated salts, DNA, lipids, polysaccharides, proteins, carbohydrates, and fragments thereof. Clarification techniques are known and include, but are not limited to, filtration, such as ultrafiltration, filter pressing or rotary vacuum filtration, and centrifugation. See, e.g., *Fermentation and Biochemical Engineering Handbook: Principles, Process Design, & Equipment*, ed. by Vogel and Todaro, Noyes Publications, Westwood, N.J., 1997, Chpt. 6 (filtration) and 12 (centrifugation).

Cross-flow filtration is a preferred method of broth clarification. In cross-flow filtration, the source of lactate material, also referred to herein as a slurry, is pumped tangentially across a membrane. A pressure gradient is created across the membrane to facilitate migration of the liquid (and low molecular weight compounds dissolved therein, including lactate material) through the membrane. The filtered liquid is also referred to as a clarified liquid or permeate. Cells, cell fragments and other high molecular weight debris do not migrate through the membrane and are retained in a concentrated slurry or retentate. Cross-flow filtration is preferred because it effectively separates impurities and debris having a variety of particle sizes (such as microorganism size) from the remainder of the solution. Cross-flow filtration is also effective for solutions having a variety of concentrations. The concentrated retentate from the cross flow filtration can be recycled back to the fermentation vessel.

In general, membranes capable of withstanding temperatures between about 40° C. and 100° C., and pH values between 2 and 7 are suitable. Preferably, the membrane material can also withstand chemical or thermal sterilization. Membrane materials that are suitable include both polymeric materials (polyethersulfone, polysulfone, polytetrafluoroethylene, and polyvinylidene fluoride) and inorganic materials (alumina, zirconia, stainless steel, and others). Companies that have membrane equipment suitable for this process include Koch Membrane Systems, Wilmington, Mass.; and U.S. Filter, Warrendale, Pa.

Cross-flow filtration can be performed as a one step process. In the single step process, cells and high molecular weight debris are removed from the fermentation broth using a membrane with a pore size from about 0.1 to 1.0 microns or a molecular weight cut off (MWCO) between 5,000 Da and 500,000 Da, inclusive. That is, a membrane having a MWCO of 5,000 Da can be used, a membrane having a MWCO of 500,000 Da can be used, or a membrane having a MWCO between 5,000 Da and 500,000 Da can be used. More preferably, to avoid membrane fouling, a membrane having a molecular weight cut off from 40,000 to 500,000 is used.

Preferably, a two step cross-flow filtration process is used. In the first step, large materials such as cells are removed using a membrane having a pore size greater than 500,000 MWCO. In the second step, high molecular weight debris, such as proteins and polysaccharides, are removed from the broth using a membrane having a MWCO between 300 Da and 500,000 Da, inclusive, More typically, this second step uses a membrane with a MWCO between 2,000 Da and 300,000 Da, inclusive.

The two step cross-flow filtration process is particularly advantageous for clarification of a fermentation broth. Because large cellular debris is filtered out in the first step, the membrane in the second step tends to not become clogged with cellular debris. Thus, the two step cross-flow filtration process tends to result in a longer membrane life and higher flux, particularly when the fermentation is performed using larger organisms such as yeast. The membrane modules are typically interchangeable so that the membrane pore size or MWCO can be altered as needed.

Cross-flow filtration can be run in a variety of flow configurations. For example, cross-flow filtration processes can be run either continuously or in batch mode. A variety of configurations are also suitable. A tubular configuration, in which the membranes are arranged longitudinally in tubes similar to the tubes in a shell and tube heat exchanger, is preferred because it can process solutions which include a variety of particle sizes (such as microorganisms). However, any flow configuration (spiral wound, flat sheet, etc.) that reduces fouling of the membrane is appropriate. See, Cheryan, M., *Ultrafiltration & Microfiltration Handbook*, Technomic Publishing Co., Inc., Lancaster, Pa., 1998, Chpt 5.

VI. Concentration I

A concentration step is optionally performed before and/or after acidulation. The concentration step can also be performed before and/or after the clarification step. Concentrating the source of lactate material tends to increase the yield of lactic acid obtained during extraction. Typically, a source of lactate material obtained by fermentation includes about 5 wt % to 15 wt %, more typically 8 wt % to 15 wt % lactate material. However, the concentration of lactate material can vary as the pH of the fermentation broth decreases, the carbon source changes, or the microorganism changes. The concentration step involves exposing the source of lactate material to an elevated temperature to reduce the volume of the solution without substantially reducing the amount of lactate material present in the solution. Typically, the volume of the solution is reduced by about 10 wt %, more preferably by about 25 wt %, most preferably by about 75 wt %, without a similar reduction in the amount of lactate material, e.g., while reducing the amount of lactate material by only about 10 wt %, more preferably by about 5 wt %, most preferably by about 0.1 wt % about 1 wt %. Typically, a concentration step provides a solution having concentration of lactate material of about 12 wt % to about 60 wt %, preferably about 12 wt % to about 30 wt %, most preferably about 15 wt % to about 25 wt %.

Generally, the concentration step is performed at an elevated temperature to improve retention of lactate material in solution, particularly when fermentation is performed at a neutral pH and the lactate material is predominantly in a salt form. Typically, the concentration step is performed at a temperature between about 60° C. and 150° C, more preferably about 70° C. to about 100° C.

Concentration can be accomplished by evaporation, pervaporation, reverse osmosis, or any other method where water is preferentially separated from the lactate material. A preferred method is the use of multiple effect evaporators. The use of multiple effects in series can evaporate of thousands to hundreds of thousands of pounds per hour of water. Multiple effect evaporators use heat generated by condensation in one effect to provide re-boiler heat for another effect. In most multiple effect units, the overhead vapor from one effect is condensed directly on the heating element of the next effect. A variety of heating unit styles can be used, from tubes to plates to mechanically agitated thin-film devices.

Preferably, the heating units reduce the thermal history of the broth (i.e., the amount of heat the broth is exposed to in terms of time and temperature). Reducing the thermal history tends to reduce thermal degradation of impurities and racemization of lactic acid. Thermal degradation of impurities generally increases the color of the solution and may result in additional separation steps being required to increase the lactic acid purity. As discussed earlier, the chiral purity of the tactic acid is important for some applications, and increased racemization associated with the concentration step may make the lactic acid inappropriate for some commercial applications.

Falling film evaporator or rising film evaporators can reduce residence time and thus reduce thermal degradation and racemization. A forced circulation evaporator may be desirable because it can process slurries (where salts may precipitate out) and viscous fluids. In contrast, a falling film or rising film evaporator may be less suitable for use with a slurry from which lactate salt may precipitate. Additionally, a thermal recompression evaporator or a mechanical recompression evaporator may be appropriate.

As the concentration of lactate material increases, the maximum solubility of calcium lactate (or other lactate salt) may be reached, resulting in the precipitation of lactate salts out of solution. Although precipitation of lactate salts typically does not reduce the quality of the purified lactic acid solution, it is preferred that the lactate salts remain in solution. Therefore, the process preferably concentrates the solution up to, but not beyond the solubility limit of the lactate salts. U.S. Pat. No. 5,766,439, incorporated by reference herein, reports the solubility of calcium lactate at varying temperatures.

Table 1 shows the percent lactic acid recovered from a four theoretical stage extraction using a solvent which includes 54 wt % Alamine 304 (Cognis, Tuscon, Ariz.) and 46 wt % Isopar K (Exxon) at 50° C. for sources of lactate material having varying concentrations. In the four stage theoretical extraction, the weight ratio of entering organic phase to entering aqueous phase was 2.5. As shown in Table 1, the amount of lactic acid recovered is greatly dependent upon the concentration of lactic acid in the source. Thus, concentrating the source of lactate material prior to lactic acid extraction improves the efficiency of the process.

TABLE 1

Lactic acid recovery from the aqueous broth

| Lactic Acid Concentration in Feed to Extraction (wt %) | % Lactic Acid Recovered in Organic Solvent |
|---|---|
| 10 | 56.5 |
| 20 | 77.2 |
| 30 | 87.5 |
| 40 | 92.4 |
| 50 | 95.3 |
| 60 | 97.4 |

Figure 3:
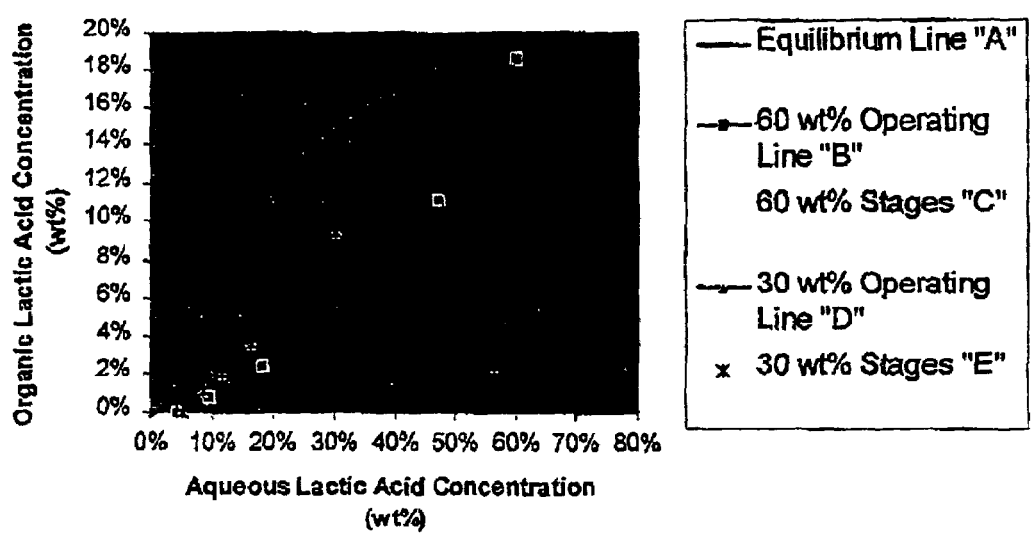
FIG. 3 is a plot showing a McCabe-Thiele diagram for the extraction of lactic acid in an amine extractant.

FIG. 3 shows a McCabe-Thiele diagram for lactic acid extracted using an organic solvent which includes 54 wt % Alamine 304 and 46 wt % IsoPar K at 50° C. Line A is the equilibrium line which shows the partitioning of lactic acid between an aqueous and an organic phase. The equilibrium line is experimentally determined by measuring the partitioning of lactic acid between the two phases. The shape of the equilibrium curve for lactic acid is usual. The curve has a relatively low slope at low lactic acid concentrations in the aqueous phase ([Lactic acid]<10 wt %). The slope increases at intermediate lactic acid concentrations in the aqueous phase (10 wt %<[Lactic acid]<21 wt %) and flattens out again at the highest aqueous lactic acid concentrations measured (21 wt %<[Lactic acid]).

Lines B and D are operating lines and stages for two sources of lactic acid having different initial lactic acid concentrations. The operating line is a measure of the ratio of aqueous phase to organic phase at any stage of the extraction. Operating lines generally become straight when the partitioning solute (lactic acid) is dilute and aqueous phase has very low solubility in the organic phase, and vice versa operating lines generally become more curved as the solute becomes more concentrated and as the solubility of the aqueous phase in the organic phase increases, and vice versa.

Generally, the operating line becomes curved because the weight ratio of the aqueous phase to the organic phase changes rapidly as the source of lactic acid becomes more concentrated. Generally, the amount of aqueous phase decreases and the amount of organic phase increases as lactic acid is extracted from the aqueous phase into the organic phase. This is due, in part, to the co-extraction of the aqueous phase into the organic phase along with the lactic acid. Additionally, movement of lactic acid from the aqueous phase into the organic phase increases the mass of the organic phase while decreasing the mass of the aqueous phase.

Operating lines B and D are not linear due to the high concentration of lactic acid and the partitioning of water into the organic phase. Line B is the operating line for a source of lactic acid having an initial lactic acid concentration of 60 wt %. Line D is the operating line for a source of lactic acid having an initial lactic acid concentration of 30 wt %. Note that at lower initial lactic acid concentrations (e.g., 30 wt % versus 60 wt %), the operating line becomes more linear.

Lines C and E show the stages of a multistage extraction for the extraction of the sources of lactic acid shown in lines B and D, respectively. Each "step" of lines C and D represent one stage of four stage theoretical extraction.

As shown in FIG. 3, a pinch point is located around 10 wt % lactic acid in the aqueous phase. Generally, the pinch point in the equilibrium curve tends to result in a decrease in lactic acid recovery because more stages are required. However, the operating line for the source of lactic acid having a higher initial lactic acid concentration (line B) is curved favorably to reduce the effect of the pinch point. Thus, in a multistage extraction of a source of lactic acid having a lower initial lactic acid concentration (line D), the extraction stages become smaller and more frequent (line E). In contrast in a multistage extraction of a source of lactic acid having a higher initial lactic acid concentration (line B), the extraction stages remain larger and less frequent (line C).

The process is also suitable for use in connection with a solvent in which the equilibrium curve does not have a pinch point. For example, when an enhancer like octanol or tributylphosphate is added to the organic solvent, the equilibrium curve tends to become more linear. The process still provides an efficient extraction of lactic acid from a solvent which includes an enhancer.

In addition to the advantages the concentration step provides when used in combination with the extraction step, the concentration step provides benefits to the overall process. The concentrating step allows solutions having uniform concentrations to be produced, regardless of the concentration of the source of lactate material. Without a concentration step, subsequent separation steps would have to be designed to process the lowest expected lactic material concentration. With the concentration step, the remaining processes steps can be designed to process a near constant lactate material concentration, Thus, only the clarification and concentration steps need to be flexible enough to handle varying concentrations of lactate material.

Both the clarification and concentration steps are easily adapted to process sources of lactate material having a variety of concentrations. The cross-flow filtration step for broth clarification is easily expanded if needed because a large plant is likely to use parallel filtration units and addition of another parallel is relatively inexpensive. Transmembrane pressure, feed fluid velocity, and other operating parameters can also be modified to obtain additional flux through the membrane. In the concentration step, many operating parameters can be altered to increase or decrease the amount of water evaporated. For example, the temperature of the heating media can be altered and/or the velocities of the fluid through the heat exchanger can be altered.

The concentration step also reduces the amount of material to be processed in the subsequent steps. For example, increasing the lactate material concentration from 10 wt % to 20 wt % decreases the amount of material for further processing by half. That is, a 200 lb solution containing a pre-concentration composition of 90% water (180 lb water) and 10% lactic acid (20 lb) can be concentrated to a 100 lb solution which contain 80% (80 lb) water and 20% (20 lb) lactic acid. The reduced volume of material to be processes substantially reduces equipment costs. Additionally, decreasing the volume of material to be processed reduces heating and cooling costs in subsequent steps.

Concentrating the source of lactate material also helps reduce the amount of impurities present in the source of lactate material. For example, some impurities in the source of lactate material may be volatile carboxylic acids (e.g. acetic acid), which, in their free acid form, can be removed from the solution by evaporation. Other impurities may have limited water solubility. For example, a contaminating acid may be less water soluble in its salt form (particularly as calcium salts). Other contaminating acids may be less soluble in their free acid form. Such contaminating acid impurities may be precipitated out of solution upon concentration, either prior to acidulation or after acidulation. Consequently, the amount of impurities in the source of lactate material may be reduced.

When the source of lactate material is concentrated prior to extraction, solvent usage is more efficient. For example, about one mole of acid is typically extracted per mole of amine in the solvent. In contrast, the present process extracts about 2 or more moles of lactic acid per mole of amine. This results in reduced solvent flow rates and thus in reduced equipment costs and reduced solvent losses. Although exceeding a molar ratio of 1:1 amine to acid ratio in many extraction processes may result in decreased selectivity, high selectivity and loading is still possible using the present method.

When the source of lactate material is concentrated, the concentration of lactic acid in the loaded solvent tends to increase as does the concentration of lactic acid in the aqueous solution obtained by back extraction. Thus, the costs associated with a final concentration step, if desired, are typically diminished. Furthermore, increasing the concentration of lactic acid tends to increase the yield of lactic acid obtained during back extraction, particularly when the solvent contains a limited amount or no enhancer. Consequently, loss of lactic acid in the lean solvent is reduced.

While concentrating the source of lactate material provides many advantages as described above, it may also increase the concentration of impurities. However, the process can still produce a purified lactic acid solution at high yields, even with increased impurity concentration.

VII. Acidulation

The source of lactate material is acidulated to convert the lactate material in the source of lactate material from its dissociated or salt form to an undissociated acid form. One method for converting lactate salt in the fermentation broth to free lactic acid is by the addition of a strong mineral acid, such as sulfuric acid, to the concentrated solution. When sulfuric acid is added to the clarified broth, free lactic acid is formed as well as a sulfuric salt. Preferably, the concentrated solution of lactate material contains calcium lactate such that lactic acid and calcium sulfate (gypsum) are formed upon addition of sulfuric acid. Gypsum is only slightly soluble in water and is easily removed from solution, for example, by crystallization.

Preferably, acidulation is performed under process conditions that favor formation of large calcium sulfate crystals. For example, acidulation is preferably performed while agitating the solution to reduce secondary nucleation. Sulfuric acid is preferably added in a manner that reduces local high superstaturation to reduce primary nucleation. Techniques for making large crystals are known and described, for instance, in U.S. Pat. No. 5,663,456, incorporated herein by reference.

Sulfuric acid added to the clarified fermentation broth at a stoichiometric ratio of sulfuric acid to lactate salt effective to convert lactate salt to lactic acid. Typically, the sulfuric acid to lactate salt ratio is between 0.90 and 1.20, preferably between 0.95 and 1.05, and most preferably 0.99 and 1.01. If other carboxylic acids, no acids or carboxylic acid functional groups are present as impurities, a higher ratio of sulfuric acid to lactate salt may be used to acidulate the impurities as well as the lactic acid.

Sulfuric acid is preferably added to the source of lactate material in a single step. However, sulfuric acid addition is preferably performed in a two step process. In the first step, a large proportion, for example about 80% to 95%, by volume, of the sulfuric acid is added to the broth and agitated. The slurry of acidified lactic acid and calcium sulfate is then transferred to another tank. In the second step, sulfuric acid is carefully metered into the system to obtain the desired stoichiometric ratio of sulfuric acid to lactate salt.

Sulfuric acid acidulation is suitable for purifying lactic acid from a source of lactate material having a pH within the range of 0.8 g to 9.0. However, for a source of lactate material having a low pH, the amount of sulfuric acid required tends to decrease. Thus, the chemical cost for acidulation tends to decrease. Furthermore, a source of lactate material having a low pH tends to produce less gypsum and thus tends to decrease salt disposal issues.

VIII. Gypsum Removal

As described above, the lactate salt in the clarified source of lactate material may be converted to lactic acid by sulfuric acid acidulation. Addition of sulfuric acid to the clarified broth also results in the production of a sulfate salt. At least some of the sulfate salt, for example, calcium sulfate or gypsum, is removed from the clarified broth to provide a purified lactic acid solution. Preferably the amount of sulfate salt present in the source of lactate material is reduced by at least about 10 wt % (by weight of the sulfate salt), preferably by about 50 wt % to about wt % (by weight of the sulfate salt), more preferably by about 90 wt % (by weight of the sulfate salt), most preferably by about 98 wt % (by weight of the sulfate salt), resulting in a solution containing no more than about 5 wt % sulfate salt (by weight of the solution), preferably, no more than about 1 wt % sulfate salt (by weight of the solution).

Methods for the filtration of gypsum are known. For example, a rotary drum vacuum filter, belt filter, or press filter can be used to reduce the amount of gypsum present in the broth. Centrifugal separators or decanters can also be used. See, e.g., *Fermentation and Biochemical Engineering Handbook: Principles, Process Design, & Equipment*, ed. by Vogel and Todaro, Noyes Publications, Westwood, N.J., 1997, Chpt. 6 (filtration) and 12 (centrifugation).

IX. Reducing the Amount of Residual Calcium Sulfate

Because residual calcium sulfate (e.g., calcium sulfate remaining after gypsum removal) in solution can cause scaling in the equipment used in subsequent processing, particularly if a subsequent concentration step is performed, it may be desirable to reduce the amount of residual calcium sulfate in the lactic acid solution. Preferably, at least some of the residual calcium sulfate is removed by additional processing. More preferably, the amount of residual calcium sulfate is preferably reduced such that the solution then includes no more than about 1 wt % calcium sulfate (by weight of the solution), preferably no more than about 0.5 wt % calcium sulfate (by weight of the solution), most preferably no more than about 0.1 wt % calcium sulfate (by weight of the solution). The residual calcium sulfate can be removed by ion exchange. In an ion exchange process, calcium ions in the lactic acid solution are removed by contact with an ion exchange resin which replaces the calcium ions with hydrogen, sodium or potassium ions. Examples of suitable cation exchange resins include the Amberlite ion exchange resins (Amberlite IR120 for instance) from Rohm and Haas, Philadelphia, Pa. and Dowex ion exchange resins (Dowex Marathon C for instance) from The Dow Chemical Company, Midland, Mich. The sulfate can then be removed by an anion exchange process. The sulfate ions are removed by contact with an anion exchange resin which replaces the sulfate with hydroxyl ion. Examples of suitable anion exchange resins include Amberlite and Dowex ion exchange resins mentioned above.

Alternately, the amount of residual sulfate can be reduced by a sulfate pre-extraction process. The same organic solvent can be used for both lactic acid extraction and sulfate pre-extraction. For example, the tertiary amine solvents described later in this application are strongly selective towards sulfuric acid over lactic acid. Therefore, the sulfate ion can be extracted from the lactic acid solution by contacting the solution with an organic phase which includes 30 to 80 wt % long chain tertiary amine, 30 to 70 wt % kerosene, and 0 to 20 wt % polar organic enhancer. The amine solution is typically added to the lactic acid solution after calcium ions are removed such that there is about a 1.0:1.5 to 0.8:1.0 molar ratio of tertiary amine to sulfate ion. The organic phase may be washed with a small amount (e.g., about 1 wt % to about 10 wt %) of an aqueous solution to recover co-extracted lactic acid. Then organic solvent can be regenerated by contacting the sulfate loaded solvent with a basic aqueous solution. This is discussed in more detail in the section labeled XV. Lean Solvent Wash.

The residual sulfate in the lactic acid solution can be controlled by the amine to sulfate ratio. This is particularly useful because residual sulfate in the lactic acid solution during extraction can function as an enhancer (see Section XII).

Typically, only a single contacting stage is necessary to reduce the amount of residual sulfate. Mixer-settlers and centrifugal extractors are preferred since they have one stage. However, the amount of residual sulfate can be reduced using a multistage or countercurrent process having multiple columns, batteries of mixer-settlers, or centrifugal extractors.

The amount of residual sulfuric acid can also be reduced during the step of back-extraction. Whereas both sulfuric acid and lactic acid are co-extracted during the amine extraction (see Section XI), only lactic acid is back-extracted in the aqueous back-extraction (see Section XV) due to the high selectivity of the amine extractant for sulfuric acid. The amount of residual sulfuric acid in the lean solvent can be reduced during a lean solvent wash (see Section XV).

Other separation steps may be suitable for reducing the amount of residual calcium sulfate in the lactic acid solution. For example, nanofiltration may be able to selectively separate lactic acid from divalent ions like calcium and sulfite. Nanofiltration also tends to remove other high molecular weight impurities like disaccharides and oligosaccharides or thermal decomposition products. Electrodialysis could be used to remove the calcium and sulfate. However, electrodialysis tends to work best with monovalent ions.

X. Concentration II

A second concentration step can optionally be performed after acidulation, for example, if a sufficient concentration of lactic acid is not obtained in the first concentration step, for example, due to the presence of insoluble calcium lactate salt. Advantageously, after acidulation, the solution contains mostly lactate material in an acid (undissociated) form. The undissociated acid form of lactate material is more soluble and therefore this concentration step is not limited by the solubility of the lactate salt. Typically, the solution of lactic acid is concentrated to about 20 wt % to about 70 wt %, more typically about 40 wt % to about 60 wt % lactic acid. Suitable concentration techniques are described above.

XI. Lactic Acid Extraction

After the amount of sulfate salt in the lactic acid solution is reduced, some impurities, such as amino acids and carbohydrates, may still remain. The purified lactic acid solution is preferably prepared by extracting the lactic acid solution with a water insoluble amine based solvent, which is also referred to as an amine solvent, organic phase, extractant or extracting solvent. The lactic acid extraction, results in the partitioning of lactic in the extractant to form a lactic acid loaded extractant, which is also referred to in the following as loaded amine solvent, loaded extracting solvent, or loaded organic phase.

The choice of the extraction solvent is important to the overall efficiency and economics of the separation process. A measure of extraction efficiency is the partition coefficient. The partition coefficient is defined as the equilibrium concentration of tactic acid in the solvent phase divided by the equilibrium concentration of free lactic acid in the aqueous phase. The partition coefficient can be calculated (after equilibration) by the concentration (wt. basis) of lactic acid in the organic phase (extractant) divided by the concentration of the lactic acid in the aqueous phase (phase from which extraction occurs). Generally, it is desirable to have a partition coefficient greater than 0.1. A partition coefficient greater than 0.5 is generally even more desirable and a partition coefficient greater than 1.0 is generally even better. The partition coefficient is affected by the choice of solvent. In commercial scale practice, extraction efficiency is related to the ability of a system to achieve a combination of high yield, low extractant volume, and concentrated product.

Preferably, extraction is conducted with a water insoluble amine. Use of an amine solvent is preferred due to favorable partitioning of lactic acid and selectivity. Preferably, the amine is immiscible in water and contains at least 18 carbon atoms. Most preferably, extraction is conducted with a tertiary amines. See for example U.S. Pat. Nos. 4,771,001; 5,132,456; and 5,510,526; and Shimizu et al, *J. of Fermentation and Bioengineering* (1996), Vol. 81 pp.240–246; Yabannavar and Wang, *Biotech Bioeng.*, (1991) Vol. 37, p. 1095–1100; and, Chen and Lee, *Appl. Biochem. Biotech*, (1997), Vol. 63–65, pp. 435–447. These six references are incorporated herein by reference.

Suitable amines include aliphatic, araliphatic or aromatic amines, or mixed aliphatic-araliphatic or aliphatic-aromatic amines, or mixtures of such amines. Examples of amines include triethylamine, dioctylamine, triotylamine, tridecylamine, methyl didodecylamine and industrial preparations such as Amberlite LA-1 (a dialkyl amine mixture with twelve carbon atoms in each alkyl chain, available from Rohm and Haas, Philadelphia, Pa.), Alamine 304 (tridodecylamine, available from Cognis, Tuscon, Ariz., formerly Henkel Corp.), Alamine 308 (a trialkyl mixture of branched chains with a total of 8 carbon atoms on each chain, available from Cognis, Tucson, Ariz.), and Alamine 336 (a mixture of trioctyl$^-$; tridecyl$^-$; dioctyldecyl$^-$ and didecyloctyl amines, available from Cognis, Tucson, Ariz.).

The temperature at which the extraction is performed can vary depending on a number of parameters, including the effect of temperature on the extraction efficiency, viscosity, and the costs cooling the extractant. Typically, the extraction is performed at a temperature between about 20° C. and about 70° C., more preferably between about 30° C. and 60° C.

Suitable equipment for contacting the two liquid phases includes packed columns, mechanically-agitated columns, perforated plate columns, pulsed columns, mixer/settlers, and centrifugal contactors. The choice of equipment may depend upon the combined flowrates of the two phases, the tendency for emulsion formation, and other operating parameters such as temperature and pressure.

The extracting solvent may also preferably contain a hydrocarbon fraction to modify the viscosity, phase coalescence, and other physical properties of the system. An example of a suitable hydrocarbon is kerosene. For example, the IsoPar family of products from Exxon are suitable kerosene products. IsoPar K is particularly preferred. The hydrocarbon is typically (if used at all) included in the extraction solvent at about 1 wt % to about 70 wt %. A preferred solvent system comprises, by wt, 30 wt % to 70 wt % Alamine 304, 0 wt % to 20 wt % polar organic enhancer such as octanol or tributyl, phosphate, and 30 wt % to 70 wt % kerosene. In solvent compositions with low enhancer concentration, a second organic phase may form during the extraction of lactic acid. Generally, the second organic phase includes a high concentration of lactic acid. However, the presence of a second organic phase could cause some operational difficulty.

The solvent used for lactic acid extraction may be obtained from another lactic acid process and therefore may contain lactic acid. For example, the solvent from a $CO_2$ driven process (described above) can be used. Preferably, the solvent contains a low concentration of lactic acid (e.g., about 1 wt % to about 5 wt %). Even though the solvent may contain some lactic acid, the solvent generally has additional extraction capacity and therefore can be used to extract lactic acid from the acidulated and concentrated solutions. If lactic acid remains in solution, it can be extracted with lean solvent. Alternately, the solution which contains the remaining lactic acid can be recycled, as described below.

Integrating the present process with another lactic acid process can reduce solvent flow rates and increase lactic acid concentrations in the solutions obtained by aqueous back extraction (described below). The reduced flow rates can reduce equipment costs, e.g., for lactic acid extraction, back extraction and evaporation, and operating costs, e.g., energy. Integration is particularly attractive in existing lactic acid production facilities because it increases capacity at relatively low cost.

Optionally, the lactic acid extraction may be designed to extract only part of the lactic acid present in the acidulated and concentrated solution, preferably between about 70 wt % and 95 wt % of the lactic acid present in the acidulated and concentrated solution. The extraction raffinate containing the residual lactic acid can then be recycled upstream, preferably prior to a concentration step, and combined with another source of lactate material. Less extraction stages tend to be required when only a part of the lactic acid present in the acidulated and concentrated solution is extracted. Additionally, solvent flow rates and capital costs also tend to be decreased.

Typically, when the raffinate is recycled, a variety of methods can be used to reduce impurities in the system. For example, a fraction of the raffinate can be purged or diverted as a waste stream. Alternately, the lactate in the raffinate can be precipitated as calcium lactate by adding lime to the solution. The calcium lactate can then be separated from the solution which can then be acidulated, preferably by acidulation, described in section VII.

XII. Enhancers

The extraction solvent can also include an enhancer to increase the partition coefficient of the lactic acid. Enhancers are especially useful when the free lactic acid concentration in the aqueous phase is low, i.e., less than 15 wt %. Generally, lactic acid partitions more strongly into the organic phase in the presence of an enhancer and more strongly into the aqueous phase in the absence of an enhancer. The enhancer is typically selected based on its enhancement strength, volatility, reactivity, or any other property required for extraction efficiency or operating ease. Typical enhancers are polar organic compounds including alcohols, ketones, esters, amides, and other polar organic liquids. A volatile enhancer is preferred because it can be distilled from the loaded solvent prior to aqueous back extraction.

Figure 4:
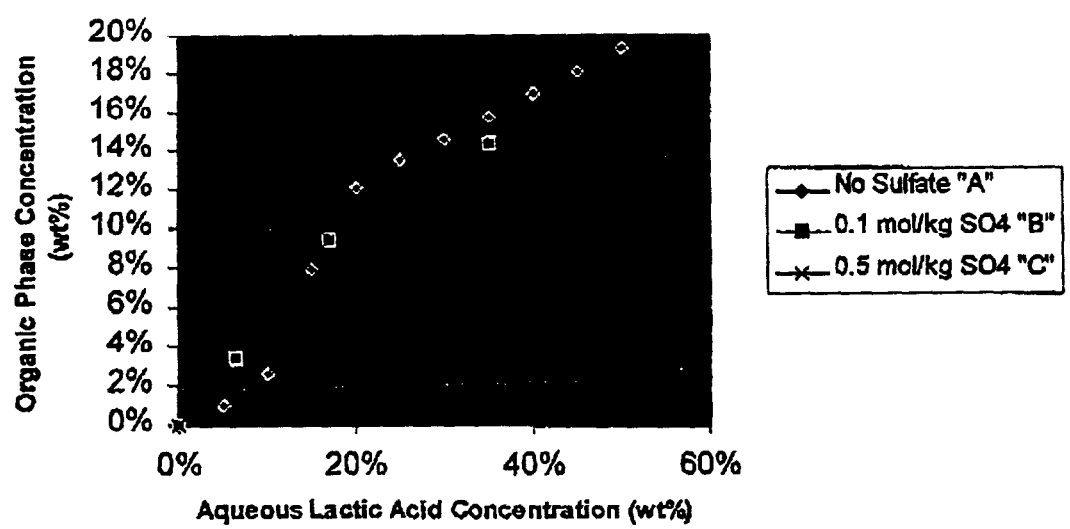
FIG. 4 is a plot showing the equilibrium curves of an amine extractant with and without sulfate present in the extract.

It has been found that sulfuric acid also acts as an enhancer and tends to increase the partitioning of lactic acid into an organic solvent, particularly an amine based solvent, more particularly a tertiary amine based solvent, at low lactic acid concentrations. Such sulfuric acid loaded amine based solvents are also referred to as sulfuric acid or sulfate containing solvents or sulfuric acid or sulfate enhanced solvents. FIG. 4 shows the equilibrium concentrations for lactic acid between water and an organic solvent which includes 54 wt % Alamine 304 and 46 wt % IsoPar K at 50° C. with and with out a sulfuric acid. Without sulfuric acid, the equilibrium curve is "S" shaped (line "A" in FIG. 4). As a result, many stages and large volumes of solvent are required to obtain a high lactic acid yield from the aqueous phase. The multiple stages and large volumes of solvent reduce the lactic acid concentration in the loaded solvent and result in low lactic acid concentration and yield in the aqueous back extraction. In contrast, when sulfuric acid is added to the organic extractant, more lactic acid partitions into the solvent phase at low lactic acid concentrations (line "B" and "C" in FIG. 4). Line "B" and "C" are the equilibrium curves when 0.1 mol/kg and 0.5 mol/kg sulfuric acid, respectively, were added to the extractant. Thus, a more efficient extraction is possible (fewer stages, higher yield, less solvent).

Table 2 shows the percent lactic acid recovered in a four theoretical stage extraction of lactic acid using a solvent containing 54 wt % Alamine 304 and 46 wt % IsoPar K at 50° C. for extractions containing 0.1 mol/kg sulfate and no sulfate. The weight ratio of entering organic phase to entering aqueous phase was 2.5. Table 2 shows the greatly increased extraction efficiency upon the use of sulfate as the enhancer.

TABLE 2

Lactic acid recovery

| Lactic Acid Concentration in Feed to Extraction (wt %) | Lactic Acid Recovery for No Sulfate Extraction | Lactic Acid Recovery for 0.1 mol/kg Sulfate Extraction |
| --- | --- | --- |
| 10 | 56.5 | 95.2 |
| 20 | 77.2 | 96.2 |
| 30 | 87.5 | 97.1 |
| 40 | 92.4 | 97.7 |

Additionally, it has been found that the sulfate anion does not back extract into an aqueous stream, even at temperatures greater than 60° C. As shown in Examples 2f and 2g, lactic acid product streams obtained from high temperature back extractions show non-detectable levels of sulfate anion.

Sulfate as an enhancer has many benefits compared to other enhancers. Most enhancers are polar organic liquids that have some volatility and solubility in an aqueous solvent and may contaminate the lactic acid solution such that additional costs may be incurred in removing the contamination from the solvent. Additionally, most enhancers degrade or become reactive at high temperatures. In contrast, sulfate has excellent thermal and reactive stability.

Preferably, the sulfate enhanced solvent contains between about 0.01 mole/Kg and about 1.0 mole/Kg sulfate, more preferably between about 0.05 mole/Kg and about 0.5 mole/Kg sulfate. Most preferably, polar organic enhancers are not added to the sulfate enhanced solvent such that the amount of polar organic material in the sulfate enhanced solvent is less than about 5 wt %, more preferably less than about 1 wt %.

A sulfuric acid loaded solvent can be obtained in a variety of ways. For example, the sulfuric acid loaded solvent can be obtained by adding sulfuric acid directly to the amine based solvent (e.g., the sulfuric acid is not residual sulfuric acid from a prior processing step) prior to or during the step of extracting. Alternately, the sulfuric acid in the amine based solvent can also be residual sulfuric acid from the acidulation step, particularly if the sulfuric acid is added in excess during the acidulation step.

Alternately, the sulfuric acid in the amine based solvent can be residual sulfuric acid from regenerating a cation exchange resin. The sulfuric acid loaded solvent can be generated in the back-extraction step (as described in section IX. Essentially, lactic acid and sulfuric acid are co-extracted during the organic solvent extraction. However, sulfuric acid tends to be retained in the organic extractant, during the aqueous back extraction due to the high selectivity of the organic extractant for sulfuric acid whereas lactic acid tends to be back-extracted during the aqueous back-extraction. The sulfuric acid loaded solvent may be used in a subsequent extraction step with or without further treatment. If desired, the amount of sulfate in the organic solvent can be controlled by a small by-pass around an anion exchange column or by controlling the amount of sulfate removed during solvent wash (discussed later).

XIII. Removal of Impurities from the Loaded Solvent

After the lactic acid solution is extracted with an amine solvent, the amine solvent which includes lactic acid can be referred to as a "loaded" solvent. The loaded amine solvent can be contacted with a minor amount of aqueous solution to reduce the amount of impurities in the solvent. For example, impurities may be co-extracted into the solvent with the lactic acid or introduced by entrainment. Examples of such impurities include salts, sugars or amino acids. Examples of suitable aqueous solutions include water or a dilute solution which includes lactic acid and water. An aqueous solution which includes a small amount (e.g., about 1 wt % to about 10 wt %) lactic acid tends to reduce the amount of lactic acid that back extracts into the aqueous solution. Multiple contacting stages can be used to obtain an organic phase that is virtually free of entrained and extracted impurities.

In the loaded solvent extraction, an aqueous solution can be combined with the loaded solvent, and the mixture agitated. The aqueous phase is then separated from the organic phase and removed. Suitable equipment for use in this liquid-liquid contacting step is known. Preferably a centrifugal extractor is used to reduce entrainment of the aqueous phase.

In determining the amount of aqueous solution used in the loaded solvent extraction, the increase in purity is typically balanced with the amount of lactic acid back extracted from the organic phase. The ratio of organic phase to aqueous solution can be changed to meet the amount of purification required and may vary depending upon the amount of impurities in the fermentation broth and/or the end use of the purified lactic acid solution. After the loaded solvent extraction, the aqueous solution can be disposed of as wastewater or, more preferably, recycled back into the process. More preferably, the aqueous solution is recycled into the acidified, clarified solution fed to the lactic acid extraction step.

XIV. Stripping

To obtain a purified lactic acid solution, the lactic acid is "stripped" from the loaded organic amine based solvent. After lactic acid is stripped from the loaded solvent, the solvent may be referred to as a "lean" solvent. Stripping the lactic acid from the solvent can be achieved by a variety of known methods, for example, back extraction, phase-splitting, membrane separation, distillation of the solvent, distillation of the lactic acid product, crystallization of the lactic acid product, and aqueous extraction. These stripping methods are described in detail in WO 99/19290, incorporated by reference herein.

Preferably, a purified lactic acid solution is obtained by extracting the lactic acid from the organic phase into an aqueous phase. Transferring the lactic acid to an immiscible liquid phase, which is relatively inexpensive, allows the amine solvent, which is relatively expensive, to be recycled.

Preferably the back extraction is performed at a temperature higher than the temperature of the extraction of lactic acid into the organic phase so that the equilibrium partitioning of lactic acid between the amine-based organic phase and water becomes more favorable towards the water, for example, see U.S. Pat. No. 4,275,234 (incorporated by reference herein). An increase in back extraction temperature tends to increase the concentration of extracted acid in the aqueous solution. However, increased back extraction temperatures may degrade the solvent components and/or the lactic acid. Because the source of lactate material is concentrated prior to extraction and, particularly if the polar organic enhancer content of the solvent is low (e.g., less than about 5 wt %, more preferably less than about 1 wt %), high back extraction temperatures (e.g., temperatures above about 120° C.) are generally not required.

Typically, the back extraction is performed at a temperature about 20° C. to about 160° C. higher than the temperature of the lactic acid extraction, more typically about 40° C. to about 100° C. higher. For example, if the lactic acid extraction is performed at a temperature of about 15° C. to about 60° C. and at atmospheric pressure, the subsequent aqueous back extraction is typically performed at a temperature of at least about 70° C., more typically at least about 100° C. As the temperature is increased above 100° C., the aqueous back extraction is typically performed under pressure, typically using nitrogen.

It may be desirable to reduce the amount of polar organic enhancer in the extracting solvent, for example, by distillation, before extracting the lactic acid in the aqueous back extraction. Generally, removal of the enhancer tend to result in a more favorable partitioning of the lactic acid into the aqueous phase.

The water used in the aqueous back extraction can also include a basic compound to increase the distribution of lactic acid in the aqueous phase, such as sodium hydroxide, ammonium hydroxide, or calcium hydroxide. U.S. Pat. No. 4,771,001 (incorporated herein by reference) discloses the use of trialkyl tertiary amines in an organic solvent with back extraction into an aqueous phase (with a relatively strong base such as ammonia).

Alternately, a two step back extraction can be performed. In the first step, the extracted acid from the organic phase is extracted with water to obtain a solution having a concentration of lactic acid greater than 30 wt %. The first step preferably uses only about 1–3 stages and has a ratio of organic phase to aqueous phase greater than 2. This first step generally recovers about 60 wt % to about 90 wt % of the lactic acid from the organic phase. In the second step, the remaining lactic acid is recovered from the organic phase by contacting the organic phase with a basic solution, such as sodium hydroxide, to obtain a lactate salt, such as sodium lactate. A two step back extraction may be preferred where some lactate salt production is desired and in production facilities which have salt-splitting capabilities. A two step back extraction also tends to have lower capital costs (fewer contacting stages) and operating costs (lower product concentrating costs).

The equipment suitable for the forward extraction as listed above is also appropriate for use in the back extraction.

XV. Lean Solvent Wash

After the lactic acid is partitioned to the aqueous phase, the lean organic solvent (e.g., the organic solvent from which at least some of the lactic acid has been extracted) is preferably washed to reduce the amount of impurities and then recycled. Typically, if a lean solvent wash is not performed, the solvent eventually emulsifies and becomes unusable. In the lean solvent wash, the solvent is combined with a solution which includes a base, such as sodium hydroxide, ammonium hydroxide or potassium hydroxide. Preferably, the lean solvent wash is a caustic (sodium hydroxide) wash, for example, using 5% sodium hydroxide. Impurities such as sulfate and chlorine partition into the basic solution along with amine degradation products. The basic phase is then removed and disposed of as a waste stream. All of the organic phase or just a portion of the organic phase can be run through the lean solvent wash depending upon the amounts of impurities in the solvent, the phase coalescence characteristics, and solvent degradation rates.

When sulfate is used as an enhancer in the extraction step, the caustic wash provides a mechanism for sulfate to be removed from the solvent.

XVI. Purified Lactic Acid Solution

The process provides a cost effective method for obtaining a purified lactic acid solution from a source of lactate material such as a fermentation broth. Whereas a fermentation broth typically contains substantial amounts of impurities, the purified lactic acid solution contains only a minor amount of impurities. For example, a fermentation broth typically contains about 5 g/L to about 40 g/L impurities, such as intact cells, cellular debris, nutrient media including a carbon and nitrogen source, heavy metals, metabolic by products, and inorganic salts. In contrast, the purified lactic acid solution typically contains no cells or cellular debris and small amounts of impurities. Generally, the purified lactic acid solution includes no more than about 1.0 g/L total nitrogen, more preferably no more than about 0.5 g/L total nitrogen and no more than about 1 g/L total carbohydrate, more preferably no more than about 0.5 g/L total carbohydrate. However, the desired impurity profile of the purified lactic acid solution may vary depending on the desired use of the solution. Preferably the purified lactic acid solution contains between about 5 wt % to about 90 wt % lactic acid, more typically between about 10 wt % to about 90 wt % lactic acid, most typically between about 20 wt % to about 50 wt % lactic acid; an aqueous carrier; and no more than about 1.0 g/L to about 5.0 g/L impurities, more preferably no more than about 0.005 g/L to about 1.0 g/L impurities, such as, proteins, carbohydrates, cellular debris, etc.

The purity of the purified lactic acid solution can be evaluated using a heated color test (See Example 1). In the heated color test, the color of a solution is determined before treatment by measuring the Yellowness Index of the solution The Yellowness Index value is reflective of the relative purity of a solution. The actual Yellowness Index values for any given lactate material sample and the resulting purified lactic acid solution may vary depending on the composition of the source of lactate material and the operating parameters of the purification process. For instance, many bacterial fermentations require complex nutrient sources that cause Yellowness Index values to be higher than the Yellowness Index values for some yeast or fungi fermentations that do not require complex nutrients.

Generally, an impure sample, such as an unprocessed fermentation broth sample will have a Yellowness Index value of about 30 to about 150, more typically about 40 to about 90. In contrast, the purified lactic acid solution sample will typically have a Yellowness Index value of about 5 to about 30, more typically about 10 to about 25. After the Yellowness Index value is measured, the sample is heated at about 140° C. to about 180° C., more preferably about 140° C. to about 160° C. for about 60 minutes to about 180 minutes, more preferably about 100 minutes to about 120 minutes. After the heat treatment, an impure solution, such as an unprocessed fermentation broth sample will have a Yellowness Index value of about 60 to about 300, more typically about 70 to 200. In contrast, the purified lactic acid solution sample after heat treatment will typically have a Yellowness Index value of about 10 to 150, more typically 10 to 100.

The Yellowness Index values for the fermentation broth and the purified lactic acid solution, before and after heat treatment, can be compared. Typically, the ratio of the Yellowness Index values for the fermentation broth sample to the purified lactic acid solution sample is about 1.2 to 20.0, more typically 1.5 to 8.0.

XVII. Uses for the Purified Lactic Acid Solution

The purified lactic acid solution is an aqueous solution that is suitable for a variety of end uses. For example, the purified lactic acid solution can be concentrated to form an 88% aqueous solution. Alternately, the purified lactic acid solution can be used to form lactate esters such as ethyl lactate or stearoyl lactate. The purified lactic acid solution can also be used to form 1,2-propanediol or acrylic acid. The purified lactic acid solution can be further processed to reduce impurities, for example, by cation exchange, anion exchange, ion exclusion chromatography, evaporation, distillation, ultra filtration, nanofiltration, carbon treatment, electrodialysis, adsorption, extraction, and/or combinations thereof.

EXAMPLES

The invention will be further described by reference to the following examples. These examples illustrate but do not limit the scope of the invention that has been set forth herein. Variation within the concepts of the invention will be apparent.

Example 1

Color Test 1600 g of fermentation broth (pH=6.0) containing 8.4 wt % calcium lactate was concentrated to 21.0 wt % calcium lactate using a rotary evaporator under reduced pressure. The 21.0 wt % calcium lactate broth was acidulated using 95.5 with sulfuric acid at a 1.02/1.0 molar ratio of sulfuric acid to calcium lactate. The calcium sulfate was filtered from the acidulated broth. The acidulated broth was then concentrated to 35.6 wt % lactic acid. This concentrated acid was extracted with an organic exit comprised of 54 wt % Alamine 304-1 and 46 wt % Isopar K at 22° C. using two crosscurrent stages. The overall ratio of organic phase to aqueous phase (O/A) was 0.96 on a volume basis. The loading in the extractant phase was 13.2 wt % lactic acid and the raffinate had a loading of 27.7% lactic acid. The loaded extractant phase was back extracted with deionized water at 100° C. The phase ratio for this operation was O/A of 0.78 on a volume basis. The loading in the aqueous product was 5.0 wt % lactic acid and the loading in the depleted organic stream was 5.7 wt % lactic acid.

The color was measured across the process described in the above paragraph. The color was measured in the initial fermentation broth and again in the aqueous back extraction product. The color was measured using a Hunter Colorimeter and the results were expressed in Yellowness Index units. The color was measured for the samples mentioned above "as is" and also after heating process for a specified amount of time. The results are listed below.

| Sample | YI | YI (heated sample) |
|---|---|---|
| Initial Broth | 90.8 | 123.1 |
| Purified Lactic Acid Product | 20.8 | 22.8 |

The heated color test is performed in the following manner:
1. Turn on oil bath and set the temperature controller to 140° C.
2. Add 70 gram of lactic acid or broth into a 100 mL round bottom flask.
3. Add 7.0 gram of glass beads to the round bottom flask.
4. Affix a 450 mm jacketed condenser onto the 100 mL flask.
5. Place the 100 mL flask into the oil bath after the oil bath temperature reaches 140° C.
6. Set the temperature controller to 160° C.
7. After the oil bath temperature reaches 160° C., allow the flask to heat for two hours.
8. After two hours, remove the 100 mL flask from the oil bath and allow it to cool to room temperature.
9. Determine color value using the Yellowness Index scale.

The method for determining the Yellowness Index is described below. This method uses a Hunter ColorQuest II Sphere colorimeter equipped with a 20 mm cell to measure yellowness index. The instrument is first standardized using a black card and a white tile to set the top and bottom of the neutral axis. The black card is used to simulate total absorption and the white tile is used to simulate total transmitance. The 20 mm sample cell containing the sample is than placed into the sample holder. The colorimeter scans the visible region of the ultraviolet spectrum and calculates the yellowness index base on the tristimulus values (X,Y,Z). The Yellowness Index is determined by integrating the visible region of the ultraviolet transmission spectrum of the sample and referencing it with the visible region of the ultraviolet transmission spectrum of the light source.

I. Preparation of Standard Check (APHA 25)
  A. Add 5 mL of 500 Platinum Cobalt standard into a 100 mL volumetric flask.
  B. Dilute to the mark using DI water.

Standardization of Hunter ColorQuest II Sphere Calorimeter Instrument
  A. Click the standardization button.
  B. Place the black tile in front of the lens and click the OK button.
  C. Place the 20 mm cell filled with DI water in the sample holder.
  D. Place the white tile in front of the reflectance port and press the OK button.

II. Preparation of Samples
  A. Rinse 20 mm cell with DI water.
  B. Filter the sample using either filter paper or a glass syringe with a 45 um filter attached to the end of it.
  C. Fill the 20 mm cell with the sample.
  D. Click the measure sample button.
  E. Enter sample name and click the OK button.
  F. Enter the yellowness index for the sample into the logbook.

III. Instrumental Conditions
  A. Illuminate: C
  B. Observer: 2°
  C. Indice: YI 1925(2/C)

IV.

V. Calibration and QC
  A. The APHA Index for the APHA 25 standard should be measured before testing samples to determine method accuracy.

VI. Calculations
  A. YI index=100 [1-(0.847*Z/Y)]

Example 2

Sulfate Enhancement

Example 2a

Lactic Acid Extraction: No Sulfate Enhancement

An extractant which includes 54% trilauryl amine, (Alamine 304, Henkel) in [?] low aromatics kerosene (Isopar K, Exxon) was prepared. 3.00 grams of the extractant solution was equilibrated with 20.00 grams of 0.75 mol/kg lactic acid aqueous solution at 50° C. The phases were settled and the lactic acid concentrations in both phases were determined. The results showed that the lactic acid partition coefficient was 0.28.

Example 2b

Lactic Acid Extraction: Sulfate Enhancement 3.051 grams of an extractant solution prepared as described in the Example 2a was contacted with 0.112 grams of an aqueous solution containing 2.95 mol/kg $H_2SO_4$. After being contacted with the extractant solution the $H_2SO_4$ concentration in the aqueous phase was below detection level. The $H_2SO_4$ loaded extractant was then equilibrated with 20.00 grams of 0.75 mol/kg lactic acid aqueous solution at 50° C., and the phases were settled. The total proton concentrations in the aqueous and in the organic phases were determined by 0.1N NaOH titraton. The lactic acid concentrations were determined by HPLC (OAKC column). The results showed that the lactic acid partition coefficient was 0.55, the concentration of the $H_2SO_4$ in the organic phase was about 0.1 mol/kg and the $H_2SO_4$ concentrations in the aqueous phases was below detection level.

Example 2e

Lactic Acid Extraction: Sulfate Enhancement

The procedure described in "Example 2b" was repeated where the amounts of the extract and that of the lactic acid solution were 3.01 grams and 20.02 grams, respectively. The amount of the $H_2SO_4$ solution was increased to 0.311 grams. The results showed that the lactic acid partition coefficient was 0.70 and the concentration of the $H_2SO_4$ in the organic phase was about 0.3 mol/kg. Again the $H_2SO_4$ concentration in the aqueous phases was below detection level.

Example 2d

The procedure described in "Example 2b" was repeated where the amounts of the extractant and that of the lactic acid solution were 3.02 grams and 20.01 grams, respectively. The amount of the $H_2SO_4$ solution was increased to 0.514 grams. The results showed that the lactic acid partition coefficient was 0.68 and the $H_2SO_4$ concentration in the organic phase was about 0.5 mol/kg. Again the $H_2SO_4$ concentration in the aqueous phases was below detection level.

Conclusion

The experiments in Example 2 show that the partition coefficient of lactic acid into the organic phase increases when sulfuric acid is present in the solvent as compared to the solvent without sulfate.

Example 3

Aqueous Back Extraction

Example 3a

Aqueous Back Extraction: No Sulfate Enhancement

An extractant that included 54% trilauryl amine, (Alamine 304, Henkel) in low aromatics kerosene (Isopar K, Exxon) was prepared. The extractant was contacted at 140° C. with aqueous solutions of lactic acid at various concentrations. The organic to aqueous phase ratio was 28:50 w/w. After equilibrium the phases were settled, the lactic acid concentrations in both phases were determined. Table 3 shows the lactic acid concentrations in both phases, and the calculated partition coefficient, Kd.

TABLE 3

| [HLa]aqueous mol/kg | [Hla]organic mol/kg | Kd |
|---|---|---|
| 1.6 | 0.155 | 0.097 |
| 2.99 | 0.337 | 0.113 |

TABLE 3-continued

| [HLa]aqueous mol/kg | [Hla]organic mol/kg | Kd |
|---|---|---|
| 3.94 | 1.12 | 0.284 |
| 4.58 | 1.53 | 0.334 |

Example 3b

Aqueous Back Extraction: Sulfate Enhancement 28 grams of the extractant, prepared as described in Example 2e, was contacted with 1.6 grams of aqueous solution containing 0.8 mol/kg $H_2SO_4$. At equilibrium, the $H_2SO_4$ concentration in the aqueous phase was below detection level. Samples of the $H_2SO_4$ loaded extractant were then equilibrated with samples containing 44–58 grams of a lactic acid solution having various concentrations at 140° C. The phases were then settled and analyzed. In all cases, the $H_2SO_4$ concentrations in the aqueous phase were below detection level. The $H_2SO_4$ concentration in the organic phase was about 0.045 mol/kg for all cases. Table 4 shows the lactic acid concentrations in both phases, and the calculated partition coefficient, Kd.

TABLE 4

| [HLa]aqueous mol/kg | [Hla]organic mol/kg | Kd |
|---|---|---|
| 3.12 | 1 | 0.321 |
| 1.47 | 0.236 | 0.161 |
| 3.82 | 1.07 | 0.280 |
| 3.21 | 0.97 | 0.302 |
| 2.11 | 0.435 | 0.206 |

Example 3c

Aqueous Back Extraction: Sulfate Enhancement 28.0 grams and 28.2 of an extractant solution prepared as described in Example 2e were equilibrated with 0.84 grams and 0.70 grams, respectively, of an aqueous solution containing 0.8 mol/kg $H_2SO_4$. Sulfuric acid concentrations in the aqueous phases were below detection level. The $H_2SO_4$ loaded extractant solutions were then equilibrated at 140° C. with 56 grams and 44 grams of an aqueous solution containing 2.1 mol/kg and 1.5 mol/kg lactic acid, respectively, and the phases were settled. The $H_2SO_4$ concentration in the organic phases was about 0.02 mol/kg and again, the concentrations of $H_2SO_4$ in the aqueous phases were below detection level. Table 5 shows the lactic acid concentrations in both phases, and the calculated partition coefficient, Kd.

TABLE 5

| [HLa]aqueous mol/kg | [Hla]organic mol/kg | Kd |
|---|---|---|
| 3.3 | 0.67 | 0.203 |
| 2.13 | 0.34 | 0.160 |

Conclusion

Example 3 shows that sulfuric acid does not partition strongly into the aqueous phase during the aqueous back extraction step. In contrast, lactic acid is efficiently back extracted into the aqueous phase.

Example 4

Purification of a Source of Lactate Material Having a Neutral pH

A lactobacillus organism is added to a fermentor containing dextrose as a carbon source. The pH of the fermenter is maintained at 6.0 by the addition of calcium hydroxide as the neutralizing agent. The continuous neutral fermentation of dextrose by the *Lactobacillus* organism provides 250,000 pounds of fermentation broth per hour.

By convention, the amount of lactate material in a solution, such as a fermentation broth can be represented by the weight percent of lactate material present if it was all in the undissociated or acid form; or the weight percent of lactate material present in the solution if it was all in the dissociated or salt form. Accordingly, when the amount of lactate material was measured as lactic acid, it was determined to be present in the amount of 10 wt % lactic acid. Alternately, when the amount of lactate material was measured as lactate salt (calcium lactate because calcium hydroxide is used as the neutralizing agent) the lactate material was determined to be present in the amount of 12.1 wt % calcium lactate.

The fermentation broth is clarified by cross-flow filtration using a 40,000 MWCO polyethersulfone membrane in a tubular configuration. The broth is then filtered by diafiltration to obtain 97% recovery of the calcium lactate. Diafiltration results in net addition of 20,000 pounds per hour water to the product stream. The clarified broth is concentrated using a mechanically recompressed evaporator under a vacuum at an internal temperature below 90° C. The evaporation step removes 120,000 pounds of water per hour. The water can be reused and/or recycled back into the process. Thus, a concentrated, clarified broth which includes 16.3 wt % lactate material (measured as lactic acid) is obtained at the rate of 149,091 pounds per hour.

In a first crystallization tank, 12,720 pounds of a 98% sulfuric acid solution is added per hour to the 16.3 wt % lactate material solution. As a result, calcium sulfate dihydrate crystallizes out of solution. The slurry (which includes the crystallized calcium sulfate dihydrate) is pumped continuously to a second crystallization tank. In the second crystallization tank, another 752 pounds of 98% sulfuric acid solution is added to the slurry per hour to further the crystallization of calcium sulfate dihydrate. The slurry is then passed to a belt filter where 24,000 pounds of water per hour is passed over the belt filter to wash the cake. 99% of the lactate material is recovered. About 32,150 pounds of 60% solids gypsum cake is obtained per hour from the filtration.

154,406 pounds of the acidulated lactic acid stream containing 15.5 wt % lactic acid and 2000 ppm residual calcium sulfate is sent to an anion and cation exchange process per hour. The ion exchange operation reduces the residual calcium sulfate down to 5 ppm. Lactic acid recovery is 98 wt %. An additional 20,000 pounds of water per hour is added to the product stream from the ion exchange operations.

A product stream of 13.6 wt % lactic acid from the ion exchange operation at a rate of 173,618 pounds per hour is then concentrated. In the concentration step, 126,563 pounds of water per hour are removed from the product stream to obtain a 50 wt % lactic acid solution at a rate of 47,055 pounds per hour.

The 50 wt % solution is contacted with 140,000 pounds of organic solvent per hour. The organic solvent includes 0.67 wt % lactic acid, 0.07 wt % water, and 53.6 wt % Alamine 304 and 45.7 wt % IsoPar K. Four theoretical extraction stages of contacting were performed in a mechanically-agitated extraction column. After the contacting step, an organic phase which includes 14.1 wt % lactic acid at a rate of 164,389 pounds per hour at was separated from the aqueous lactic acid solution. A lactic acid recovery of 94.6% was obtained in the extraction step. No loaded solvent wash was performed.

The lactic acid loaded organic phase was contacted with 24,000 pounds of water in a pressurized, mechanically agitated extraction column at 140° C. Four theoretical stages of extraction were achieved to obtain an aqueous product which included 45.3 wt % lactic acid at a rate of 47,840 pounds per hour. About 10% of the solvent stream was contacted with a 5 wt % sodium hydroxide solution at a phase ratio of 30:1 organic to aqueous (by mass).

The 45.3 wt % purified lactic acid solution product is then available for further processing as needed for its intended use.

Example 5

Purification of a Source of Lactate Material Having a Low pH

A yeast organism that has been genetically modified to produce lactic acid at a low pH is used in a batch fermentation of a mixed sugar stream. After fermentation is complete (e.g., the mixed sugar stream has been depleted), the broth is added to a holding tank. A continuous stream of fermentation broth is delivered to the downstream processing at a rate of 250,000 pounds per hour. The fermentation broth includes 8 wt % lactic acid and 2 wt % calcium lactate. The fermentation broth is clarified using a ceramic membrane with a 0.1 micron pore size. Proteins are then removed from the broth using a 10,000 MWCO polyethersulfone membrane in a spiral wound configuration. Diafiltration for both ultrafiltration processes adds an additional 25,000 pounds of water to the product stream per hour. The resulting clarified broth is concentrated using a multi-effect evaporator under vacuum. All effects are operated at a temperature below 95° C. The evaporation step removes 155,000 pounds of water per hour. The water is suitable for recycle or reuse. A concentrated broth that includes about 16.2 wt % lactate material is obtained at a rate of 139,031 pounds per hour.

1822 pounds of 98 wt % sulfuric acid is added to the concentrated broth per hour. Calcium sulfate dihydrate crystallizes out of the acidulated broth and is filtered off on a rotary drum vacuum filter. A 99% recovery of lactic acid is achieved by washing the gypsum cake with 2,400 pounds of water per hour. A 60 wt % solids gypsum cake is obtained from the filter at a rate of 3986 pounds per hour. An acidulated: lactic acid stream containing 16.0 wt % lactic acid and 2000 ppm residual calcium sulfate is obtained at a rate of 139,304 pounds per hour. The acidulated lactic acid stream is sent to a cation exchange process which replaces the calcium with protons. The ion exchange operation reduces the residual calcium in the acidulated lactic acid stream to 5 ppm with a lactic acid recovery of 99%. An additional 10,000 pound of water per hour is added to the product stream by the cation exchange process.

A product stream confiding 14.8 wt % lactic acid is obtained at a rate of 148,998 pounds per hour from the cation exchange operation. This product steam is sent to the concentration step. In the concentration step, 93,805 pounds of water are removed from the product stream per hour to obtain a 40 wt % lactic acid solution at a rate of 55,194 pounds per hour.

The 40 wt % solution is contacted with 140,000 pounds of organic solvent per hour to form a solution which includes 0.6 wt % lactic acid, 0.06 wt % water, 53.6 wt % Alamine 304 and 45.7 wt % IsoPar K. Four theoretical extraction stages are performed in a mechanically-agitated extraction column. After the contacting, an organic phase including 13.5 wt % lactic acid is separated from the aqueous lactic acid solution at a rate of 163,356 pounds per hour. A lactic acid recovery of 96.3% is obtained in the extraction step. No loaded solvent wash is performed.

The lactic acid loaded organic phase is contacted with 24,000 pounds of water in a pressurized, mechanically agitated extraction column at 140° C. Four theoretical stages of separation are performed to obtain an aqueous product which includes 44.7 wt % lactic acid at a rate of 47,174 pounds per hour. About 10% of the solvent stream is contacted with a 5 wt % sodium hydroxide solution at an organic to aqueous phase ratio of 30:1 by mass.

The 44.7 wt % purified lactic acid solution product is then available for further processing as needed for its intended use.

What is claimed is:

1. A process comprising:
   fermenting a carbohydrate to form an aqueous solution comprising calcium lactate;
   adding sulfuric acid to the aqueous solution to form a slurry of calcium sulfate in an acidulated solution;
   removing at least a portion of the calcium sulfate from the slurry;
   extracting the acidulated solution with an amine extractant to form a loaded solvent; and
   contacting the loaded solvent with a solution of lactic acid in water to reduce impurities and form a second loaded solvent.

2. A process comprising:
   providing an aqueous solution comprising calcium lactate;
   concentrating the solution;
   adding sulfuric acid to the aqueous solution to form calcium sulfate in an acidulated solution;
   removing at least a portion of the calcium sulfate from the acidulated solution; and
   extracting the acidulated solution with an amine extractant to form a loaded solvent, wherein the amine extractant includes sulfuric acid.

3. A process comprising extracting an acidulated solution comprising lactic acid with a mixture comprising an amine extractant and sulfuric acid to form a loaded solvent.

4. The process of claim 1, further comprising:
   back-extracting the second loaded solvent with an aqueous extract solution to remove lactic acid from the second loaded solvent.

5. The process of claim 4, wherein the aqueous extract solution comprises a basic compound.

6. The process of claim 4, wherein back-extracting the second loaded solvent with an aqueous extract solution comprises a two step back extraction comprising:
   back-extracting with water; and
   back-extracting with a basic solution.

7. The process of claim 1, further comprising concentrating the aqueous solution, wherein the sulfuric acid is added to the aqueous solution before concentrating the solution.

8. The process of claim 1, further comprising concentrating the aqueous solution, wherein the sulfuric acid is added to the aqueous solution after concentrating the solution.

9. The process of claim 1, wherein the slurry of calcium sulfate in an acidulated solution includes at least 12% by weight lactate material.

10. The process of claim 1, wherein the solution of lactic acid in water includes from about 1% to about 10% by weight lactic acid.

11. The process of claim 2, further comprising:
removing lactic acid from the loaded solvent.

12. The process of claim 11, wherein removing lactic acid from the loaded solvent comprises back-extracting the loaded solvent wit an aqueous extract solution.

13. The process of claim 2, wherein the amine extractant includes sulfuric acid in an amount sufficient to provide about 0.01 to about 1.0 mole/Kg sulfate.

14. The process of claim 2, wherein the sulfuric acid is added to the aqueous solution before concentrating the solution.

15. The process of claim 2, wherein the sulfuric acid is added to the aqueous solution after concentrating the solution.

16. The process of claim 2, wherein adding sulfuric acid to the aqueous solution comprises forming a slurry of calcium sulfate in an acidulated solution.

17. The process of claim 2, wherein the slurry of calcium sulfate in an acidulated solution includes at least 12% by weight lactate material.

18. The process of claim 3, further comprising removing lactic acid from the loaded solvent.

19. The process of claim 3, further comprising contacting the loaded solvent wit a solution of lactic acid in water to reduce impurities and form a second loaded solvent.

20. The process of claim 19, further comprising removing lactic acid from the second loaded solvent.

21. The process of claim 19, further comprising back-extracting with water to remove lactic acid from the second loaded solvent.

22. The process of claim 19, further comprising back-extracting with a basic solution to remove lactic acid from the second loaded solvent.

* * * * *

UNITED STATES PATENT AND TRADEMARK OFFICE
CERTIFICATE OF CORRECTION

| | | |
|---|---|---|
| PATENT NO. | : 7,026,145 B2 | Page 1 of 1 |
| APPLICATION NO. | : 10/162935 | |
| DATED | : April 11, 2006 | |
| INVENTOR(S) | : Joseph Mizrahi et al. | |

It is certified that error appears in the above-identified patent and that said Letters Patent is hereby corrected as shown below:

Column 35, line 14, please delete "wit" and insert --with--therefor;

Column 36, line 11, please delete "wit" and insert --with--therefor.

Signed and Sealed this

Third Day of October, 2006

JON W. DUDAS
*Director of the United States Patent and Trademark Office*